US009823204B2

(12) United States Patent
McClay et al.

(10) Patent No.: US 9,823,204 B2
(45) Date of Patent: Nov. 21, 2017

(54) METABOLOMICS-BASED BIOMARKERS FOR LUNG FUNCTION

(75) Inventors: Joseph Louie McClay, Richmond, VA (US); Barbara K. Zedler, Richmond, VA (US); Edward Lenn Murrelle, Midlothian, VA (US); Edwin J. C. G. van den Oord, Richmond, VA (US); Thomas O'Connell, Raleigh, NC (US); Daniel Adkins, Richmond, VA (US)

(73) Assignee: Lineagen, Inc., Salt Lake City, UT (US)

( * ) Notice: Subject to any disclaimer, the term of this patent is extended or adjusted under 35 U.S.C. 154(b) by 0 days.

(21) Appl. No.: 13/541,449

(22) Filed: Jul. 3, 2012

(65) Prior Publication Data

US 2013/0149388 A1 Jun. 13, 2013

Related U.S. Application Data

(63) Continuation of application No. PCT/US2011/020149, filed on Jan. 4, 2011.

(60) Provisional application No. 61/292,147, filed on Jan. 4, 2010.

(51) Int. Cl.
| | |
|---|---|
| G01N 33/483 | (2006.01) |
| G01N 33/493 | (2006.01) |
| G01N 33/48 | (2006.01) |
| G01N 33/50 | (2006.01) |
| G01N 24/08 | (2006.01) |
| G01N 33/574 | (2006.01) |

(52) U.S. Cl.
CPC ....... *G01N 24/08* (2013.01); *G01N 33/57423* (2013.01); *G01N 2800/12* (2013.01); *G01N 2800/122* (2013.01)

(58) Field of Classification Search
CPC .............................. G01N 24/08; G01R 33/465
See application file for complete search history.

(56) References Cited

U.S. PATENT DOCUMENTS

| | | | | |
|---|---|---|---|---|
| 7,935,518 B2 * | 5/2011 | Luchini et al. | ............ | 435/287.1 |
| 2004/0077106 A1 * | 4/2004 | Haddad | .................. | G01N 33/94 436/536 |
| 2004/0096917 A1 * | 5/2004 | Ivey | ..................... | C12Q 1/6837 435/7.32 |
| 2007/0043518 A1 * | 2/2007 | Nicholson et al. | ............ | 702/23 |
| 2009/0104596 A1 * | 4/2009 | Assadi-Porter et al. | .......... | 435/5 |
| 2010/0136600 A1 * | 6/2010 | Slupsky et al. | ................. | 435/29 |
| 2011/0311650 A1 * | 12/2011 | Wang et al. | .................. | 424/646 |

FOREIGN PATENT DOCUMENTS

| | | | |
|---|---|---|---|
| WO | WO 2005052575 A1 * | 6/2005 | |
| WO | 2008124920 A1 | 10/2008 | |

OTHER PUBLICATIONS

Snell-Burgeon, "Evaluation of Urinary Biomarkers for Coronary Artery Disease, Diabetes, and Diabetic Kidney Disease", Diabetes Technology & Therapeutics, vol. 11, No. 1, 2009.*
Lang, "Quantitative Investigation of Trigonelline, Nicotinic Acid, and Nicotinamide in Foods, Urine, and Plasma by Means of LC-MS/MS and Stable Isotope Dilution Analysis", Journal of Agricultural and Food Chemistry, 56, 11114-11121, 2008.*
Villas-Boas, "Mass Spectrometry in Metabolome Analysis", Mass Spectrometry Reviews, 24, 613-646, 2005.*
Wishart, "Metabolomics in Humans and Other Mammals", Metabolome Analysis: An Introduction, Chapter 10, pp. 253-288, 2006.*
Lightsey, "Normal Levels of Urine Creatinine & Protein", a webpage at www.livestrong.com [retrieved on Apr. 15, 2016]. Retrieved from the Internet: <URL: http://www.livestrong.com/article/417912-normal-levels-of-urine-creatinine-protein/>.*
Medlineplus, "Protein urine test", an online article at www.nlm.nih.gov [retrieved on Apr. 15, 2016]. Retrieved from the Internet: <URL: https://www.nlm.nih.gov/medlineplus/ency/article/003580.htm>.*
Anthonisen, N., et al.: "Effects of smoking intervention and the use of an inhaled anticholinergic bronchodilator on the rate of decline of FEV1: the Lung Health Study", AMA, vol. 272, pp. 1497-1505.
Baraldo, S., et al.: "Matrix metalloproteinase-2 protein in lung periphery is related to COPD progression", Chest, 2007, vol. 132, No. 6, pp. 1733-1740.
Benjamini, Y., et al.: "Controlling the false discovery rate: a practical and powerful approach to multiple testing", 1995, Journal of the Royal Statistical Society B, vol. 57, pp. 289-300.
Bernini, P., et al.: "Individual Human Phenotypes in Metabolic Space and Time", Journal of Proteome Res. 2009, vol. 8, No. 9, pp. 4264-4271.
Curtis, J., et al.: "The Immunopathogenesis of Chronic Obstructive Pulmonary Disease: Insights from Recent Research", Proceedings of the American Thoracic Society, 2007, vol. 4, No. 7, pp. 512-521.
De Laurentis, G., et al.: "Metabolomics analysis of exhaled breath condensate in adults by nuclear magnetic resonance spectroscopy", Eur. Respiratory Journal, 2008, vol. 32, No. 5, pp. 1175-1183.
Enright, G., et al.: "Prevalence and correlates of respiratory symptoms and disease in the elderly", Chest, 1994, vol. 106, pp. 827-834.
Evans, G., et al.:: "Designer science and the 'omic' revolution", Nature Biotechnology, 2000, vol. 18, No. 2, p. 127.
Feenstra, T., et al.: "The impact of aging and smoking on the future burden of chronic obstructive pulmonary disease: a model analysis in the Netherlands", American Journal on Respiratory Critical Care Medicine, 2001, vol. 164, No. 4, pp. 590-596.

(Continued)

*Primary Examiner* — Robert T Crow
*Assistant Examiner* — John P Nguyen
(74) *Attorney, Agent, or Firm* — Perkins Coie LLP (57) ABSTRACT

Chronic obstructive pulmonary disease (COPD), characterized by chronic airflow limitation, is a serious and growing public health concern. The major environmental risk factor for COPD is cigarette smoking, but the biological mechanisms underlying COPD are not well understood. Herein, proton nuclear magnetic resonance ($^{1}$H-NMR) spectroscopy is used in methods to identify metabolites and biomarkers associated with lung function in COPD.

13 Claims, 2 Drawing Sheets

(56) References Cited

OTHER PUBLICATIONS

Fernando, R., et al.: "Controlling the proportion of false positives in multiple dependent tests", Genetics, 2004, vol. 166, No. 1, pp. 611-619.

Gregory, J., et al.: "Primed, constant infusion with [2H3]serine allows in vivo kinetic measurement of serine turnover, homocysteine remethylation, and transsulfuration processes in human one-carbon metabolism", Am J Clin. Nutr., 2000, vol. 72, No. 6, pp. 1535-1541.

Griffith, K., et al.: "Predictors of loss of lung function in the elderly. The Cardiovascular Health Study", American Journal of Respiratory and Critical Care Medicine, 2001, vol. 163, pp. 61-68.

Hoidal, J.: "Genetics of COPD: present and future", Eur. Respir. Journal, 2001, vol. 18, No. 5, pp. 741-743.

Korn, E., et al.: "Controlling the number of false discoveries: application to high-dimensional genomic data", Journal of Statistical Planning and Inference, 2004, vol. 124, No. 2, pp. 379-398.

Lang, R., et al.: "Quantitative Investigation of Trigonelline, Nicotinic Acid, and Nicotinamide in Foods, Urine, and Plasma by means of LC-MS/MS and Stable Isotope Dilution Analysis".

Li, M., et al.: "Symbiotic gut microbes modulate human metabolic phenotypes", Proc.Natl.Acad.Sci.U.S.A, 2008, vol. 105, No. 6, pp. 2117-2122.

Lokke, A., et al.: "Developing COPD: a 25 year follow up study of the general population", Thorax, 2006, vol. 61, pp. 935-939.

Lundback, B., et al.: "Not 15 but 50% of smokers develop COPD? Report from the Obstructive Lung Disease in Northern Sweden Studies", Respiratory Medicine, 2003, vol. 97, pp. 115-122.

Macnee, W.: "Pulmonary and Systemic Oxidant/Antioxidant Imbalance in Chronic Obstructive Pulmonary Disease", Proceedings of the American Thoracic Society, 2005, vol. 2, pp. 50-60.

Makinen, V., et al.: "$^1$H NMR metabolomics approach to the disease continuum of diabetic complications and premature death", Molecular Systems Biology, 2008, vol. 4, Article 167, pp. 1-12.

Mannino, D., et al.: "The epidemiology and economics of chronic obstructive pulmonary disease", Proceedings of the American Thoracic Society, 2007, vol. 4, pp. 502-506.

Marsh, S., et al.: "Smoking and COPD: what really are the risks?", European Respiratory Journal, 2006, vol. 28, pp. 883-886.

Mulder, T., et al.: "Consumption of both black tea and green tea results in an increase in the excretion of hippuric acid into urine", Am J Clin. Nutr. 2005, vol. 81, No. 1 Suppl, pp. 256S-260S.

Nicholson, J., et al.: "High Resolution Proton Magnetic Resonance Spectroscopy of Biological Fluids", Progress in NMR Spectroscopy, 1989, vol. 21, pp. 449-501.

Oostendorp, M., et al.: "Diagnosing inborn errors of lipid metabolism with proton nuclear magnetic resonance spectroscopy", Clin. Chem. 2006, vol. 52, No. 7, pp. 1395-1405.

Rabe, K., et al.: "Global strategy for the diagnosis, management, and prevention of chronic obstructive pulmonary disease: GOLD executive summary", American Journal Respiratory Critical Care Med. 2007, vol. 176, No. 6, pp. 532-555.

Royston, P., "Imputation of missing values: update". Stata Journal, 2005, vol. 5, pp. 527-536.

Sabatti, C ., et al.: "False discovery rate in linkage and association genome screens for complex disorders", Genetics, 2003, vol. 164, No. 2, pp. 829-833.

Samuel, B., et al.: "A humanized gnotobiotic mouse model of host-archaeal-bacterial mutualism", 2006, Proc Natl Acad Sci, USA, vol. 103, No. 26, pp. 10011-10016.

Sandford, A., et al.: "Chronic obstructive pulmonary disease. 1: Susceptibility factors for COPD the genotype-environment interaction", Thorax, 2002, vol. 57, No. 8, pp. 736-741.

Sansone, S., et al.: "The metabolomics standards initiative", Nature Biotechnology, 2007, vol. 25, No. 8, pp. 846-848.

Storey, J.: "Statistical significance for genome-wide studies", Proceedings of the National Academy of Sciences of the United States of America, 2003, vol. 100, No. 16, pp. 9440-9445.

Storey, J.: "The positive false discovery rate: a Bayesian interpretation and the q-value, Annals of Statistics", 2003, No. 31, pp. 2013-2035.

Tang, H., et al.: "Use of relaxation-edited one-dimensional and two dimensional nuclear magnetic resonance spectroscopy to improve detection of small metabolites in blood plasma", Anal.: Biochem. 2004, vol. 325, No. 2, pp. 260-272.

Tlaskalova-Hogenova, H., et al.: "Commensal bacteria (normal microflora), mucosal immunity and chronic inflammatory and autoimmune diseases", Immunol. Lett. 2004, vol. 93, No. 2-3, pp. 97-108.

Tsai, C., et al.: "Estimation of false discovery rates in multiple testing: application to gene microarray data", Biometrics, 2003, vol. 59, No. 4, pp. 1071-1081.

Tukiainen, T., et al.: "A multi-metabolite analysis of serum by 1H NMR spectroscopy: early systemic signs of Alzheimer's disease", Biochem. Biophys. Res Commun. 2008, vol. 375, No. 3, pp. 356-361.

Van Buuren, S., et al.: Fully conditional specification in multivariate imputation. J. Stat. Comput. Sim. 2006, vol. 76, 1049-1064.

Van Den Oord, E.: "Controlling false discoveries in candidate gene studies", Molecular Psychiatry, 2005, vol. 10, No. 3, pp. 230-231.

Willett, J., et al.: "The design and analysis of longitudinal studies of development and psychopathology in context: Statistical models and methodological recommendations", Development and Psychopathology, 1998, vol. 10, pp. 395-426.

Wishart, D.: Metabolomics in Humans and other Mammals, 2007, Chapter 10, pp. 253-288.

Xia, J., et al.: "MetaboAnalyst: a web server for metabolomic data analysis and interpretation", Nucleic Acids Research, 2009, vol. 37, pp. W652-W660.

\* cited by examiner

METABOLOMICS-BASED BIOMARKERS FOR LUNG FUNCTION

CROSS REFERENCE TO RELATED APPLICATIONS

This application is a continuation of International Application No. PCT/US2011/020149, filed Jan. 4, 2011, which claims the benefit of U.S. Provisional Application Ser. No. 61/292,147, filed Jan. 4, 2010, both of which are entitled Metabolomics-Based Biomarkers for Lung Function, each of which application is herein incorporated by reference in its entirety.

FIELD OF THE TECHNOLOGY

The field of the technology provided herein relates generally to pulmonary and related diseases and diagnosis and prognosis thereof.

BACKGROUND

Chronic obstructive pulmonary disease (COPD) is the fourth leading cause of chronic morbidity and mortality in the United States and is projected to become the third leading cause of death worldwide by 2020 (Mannino & Braman 2007, *Proceedings of the American Thoracic Society*, vol. 4, pp. 502-506; Rabe et al. 2007, *Am J Respir. Crit Care Med.*, vol. 176, no. 6, pp. 532-555). Cigarette smoking is recognized as the most important environmental causative factor for COPD (Mannino & Braman 2007; Marsh et al. 2006, *European Respiratory Journal*, vol. 28, pp. 883-886; Rabe et al. 2007). It is estimated that up to 50% of smokers may eventually develop COPD, as defined by the Global Initiative for Chronic Obstructive Lung Disease (GOLD) spirometric criteria (Lokke et al. 2006, *Thorax*, vol. 61, pp. 935-939; Lundbäck et al. 2003, *Respiratory Medicine*, vol. 97, pp. 115-122; Mannino & Braman 2007). COPD is characterized by incompletely reversible airflow limitation that results from small airway disease (obstructive bronchiolitis) and parenchymal destruction (emphysema). These pathologic changes are the result of an abnormal inflammatory response to long-term exposure to noxious gases or particles, with structural changes due to repeated injury and repair (Rabe et al. 2007). The mechanisms of the enhanced inflammation that characterizes COPD involve both innate and adaptive immunity in response initially to inhalation of particles and gases (MacNee 2001, *Journal of Pharmacology*, vol. 429, pp. 195-207). Several studies have demonstrated differences in markers of inflammation and immune response, such as a correlation between the number of CD8 cytotoxic T lymphocytes and the degree of airflow limitation in COPD (Curtis, Freeman, & Hogg 2007, *Proceedings of the American Thoracic Society*, vol. 4, no. 7, pp. 512-521). The response to oxidative stress is considered an important factor in the pathogenesis of COPD (MacNee 2005, *Proceedings of the American Thoracic Society*, vol. 2, no. 1, pp. 50-60), while protease-antiprotease imbalance is thought to be associated with emphysema (Baraldo et al. 2007, *Chest*, vol. 132, no. 6, pp. 1733-1740). However, while inflammation and other factors are clearly involved in the molecular pathogenesis of COPD, the precise etiological mechanisms remain to be fully characterized.

Recent advances in laboratory technologies have enabled "omics" investigations that allow researchers to interrogate diseases on an unprecedented scale (Evans 2000, *Nature Biotechnology*, vol. 18, no. 2, p. 127). A rapidly developing discipline in this area is metabolomics, which is the study of all measurable metabolites in a given biological sample (Kaddurah-Daouk, Kristal, & Weinshilboum 2008, *Annu. Rev. Pharmacol. Toxicol.*, vol. 48, pp. 653-683). Metabolomics studies typically employ either mass spectrometry or nuclear magnetic resonance (NMR) to assay the biochemical components of a tissue or biofluid. Proton ($^1$H) NMR metabolomics has already shown considerable potential as a diagnostic tool for Alzheimer's disease (Tukiainen et al. 2008, *Biochem. Biophys. Res Commun.*, vol. 375, no. 3, pp. 356-361), diabetes and related disorders (Makinen et al. 2006, *MAGMA.*, vol. 19, no. 6, pp. 281-296; Makinen et al. 2008, *Mol Syst. Biol.*, vol. 4, p. 167) and inborn errors of lipid metabolism (Oostendorp et al. 2006, *Clin. Chem.*, vol. 52, no. 7, pp. 1395-1405). Furthermore, $^1$H NMR metabolomics can facilitate the discovery of novel candidate biomarkers of disease risk, as demonstrated by Holmes et al. (2008, *Nature*, vol. 453, no. 7193, pp. 396-400) in a recent population study of blood pressure. Finally, considering pulmonary studies specifically, de Laurentiis et al. (2008, *Eur. Respir. J*, vol. 32, no. 5, pp. 1175-1183) found that NMR-based metabolic profiles of exhaled breath condensate enabled discrimination between individuals with and without COPD.

An individual's overall 'metabolic phenotype' reflects an individual's metabolic characteristics and is determined by the interaction of an individual's genetic makeup and his/her adaptive response to the environment. As described by Bemini et al. (*J. Proteome Res.*, 2009, 8 (9), pp 4264-4271), any "differences between individual phenotypes are due both to differences in genotype and exposure to different environmental factors . . . [I]ndividual metabolic phenotype can also be considered a metagenomic entity that is strongly affected by both gut microbiome and host metabolic phenotype, the latter defined by both genetic and environmental contribution." Bernini et al. Thus, differences in cellular processes due to exposure to harmful substances are reflected as differences in metabolic phenotypes in subjects having a lung disease such as, for example, COPD as compared to normal (healthy) subjects.

The biochemical composition resulting from an individual's metabolic processes is ultimately reflected in the extracellular tissue fluid and consequently in an individual's biofluids such as blood and urine. Consequently, abnormal cellular metabolic processes can effect compositions of blood and urine. As such, these fluids may provide diagnostic and prognostic windows onto an individual's "phenotypic state". For example, in subjects having the disorder phenylketonuria (deficiency of a phenylalanine converting enzyme), increased concentration of phenylpyruvic acid, phenyllactic acid and phenylacetic acid are present in urine from such subjects as compared to urine of normal subjects. See, e.g., Text Book of Biochemistry with Clinical Correlations, 4th Edition, 1997, edited by T. M. Devin, published by Wiley-Liss. In such cases, urinary biochemical analysis can diagnose or aid in the diagnosis of those subjects having the enzyme deficiency.

In lung disorder such as, for example, COPD, factors influencing lung function and its decline include environmental and biological effects (Feenstra et al. 2001, *Am J Respir. Crit Care Med.*, vol. 164, no. 4, pp. 590-596; Hoidal 2001, *Eur. Respir. J*, vol. 18, no. 5, pp. 741-743; Sandford & Silverman 2002, *Thorax*, vol. 57, no. 8, pp. 736-741). Although factors associated with lung function decline in middle-aged and older adults have been identified in cross-sectional studies (Enright et al. 1994; Kerstjens, Brand, and Postma 1996), predictions based on such studies may not adequately predict longitudinal changes within individuals (Knudson et al. 1983, *American Review of Respiratory Disease*, vol. 127, pp. 725-734; Griffith et al. 2001, *American Journal of Respiratory and Critical Care Medicine*, vol. 163, pp. 61-68).

Prior diagnostic methods of COPD and other lung diseases employ diagnostic tests which rely on the presumed correlation of functional measures of decreased lung function with lung disease. Spirometry, which is the most commonly performed lung function test, is a simple breathing test that measures the quantity of air that a subject can expel and the speed with which the air is expelled. While lung function tests can provide a general assessment of the functional status of a subject's lungs, it does not distinguish between the different types of lung diseases that may be present. Certain diseases such as asthma for example cannot be confirmed based on functional tests alone. In addition, it is only when a change in lung function exists can such tests assist in the diagnosis of lung disease. Functional diagnostic methods do not predict the onset or progression of the disease.

In contrast to diagnostics based on lung function, proton nuclear magnetic resonance spectroscopy, as described herein, can be used to identify and quantify metabolites associated with decreased lung function without functional assessment.

SUMMARY

The present disclosure sets for the associations between lung disease, such as COPD, and variations in the quantity and type of metabolite biomarkers present in a subject's urine. The urinary metabolic profile of subjects with lung disease, such as COPD, differs from the profile of subjects not having, e.g., COPD. Embodiments described herein provide urine metabolites having significant novel associations with COPD. No such association is found with metabolites present in plasma. As described below, some of the metabolites reflect interactions between a subject's genome, diet and gut microbiome.

The present disclosure provides a method of identifying novel metabolite biomarkers of lung function. In one aspect, the method includes use of an NMR-based approach. In another aspect, the profiles are obtained using high resolution NMR. The method includes use of biomarkers that are identified by comparison of the profiles of metabolites in urine of subjects having a lung disease and subjects not having the lung disease. The novel biomarkers of lung disease are useful as diagnostic and/or prognostic indicators of lung disease or as an indicator of a subject's risk of developing lung disease. In one particular aspect, the lung disease is COPD.

In one embodiment, a metabolite biomarker includes a metabolite derived from host-gut microflora symbiosis. In another embodiment, the metabolite biomarker is selected from formate, hippurate and/or trigonelline.

In one embodiment, the present disclosure provides novel metabolite biomarkers that can be used for in vivo and/or in vitro medical diagnostics. For example, a method of diagnosing or aiding in the diagnosis of lung disease in a subject is provided, wherein the method includes use of one or more, or two or more described metabolite biomarker. In one aspect, the method includes detecting in a urine sample obtained from a subject the presence of, or measuring the level of, one or more, or two or more biomarkers. In one aspect, a metabolite biomarker of lung disease or impaired lung function includes a metabolite derived from host-gut microflora symbiosis. In another aspect, the metabolite biomarker of lung disease or impaired lung function is selected from the group consisting of formate, hippurate and trigonelline. Thus, the biomarkers provided herein can be used to distinguish a condition of lung disease or impaired lung function from a healthy non-diseased (control) condition or from a disease other than a lung disease.

Diagnosis of lung disease may include, but is not limited to, examination for the presence of one or more, or two or more, metabolite biomarkers of lung disease present or absent in a urine sample obtained from a test subject. The presence or absence of one or more metabolite biomarkers of lung disease in the test urine sample can indicate the presence of lung disease in the test subject. In one embodiment, test sample is a sample of urine from a subject whose disease status is unknown or who is suspected of having a lung disease. The control biological fluid sample may be urine from an individual or a population pool that are known to not to have lung disease or impaired lung function. A lung disease may include, for example, COPD, chronic systemic inflammation, emphysema, asthma, pulmonary fibrosis, cystic fibrosis, obstructive lung disease, pulmonary inflammatory disorder and other disease of the lung. In any embodiment lung disease may, or may not, also include lung cancer. In one embodiment, a metabolite biomarker of lung disease includes a metabolite derived from host-gut microflora symbiosis. In another embodiment, the metabolite biomarker is selected from the group consisting of: formate, hippurate and trigonelline.

In another embodiment the present disclosure provides a method for determining a subject's risk of developing a lung disease. In such a determination, the quantitative level (concentration) of one or more, or two or more metabolite biomarkers in a test sample (e.g., biofluid) is measured and compared to a known standard. A standard may be a sample of urine obtained from an individual or a population pool having a known diagnosis of a lung disease or may be a fluid sample comprising a known concentration of one or more isolated biomarkers determined to be associated with a predetermined risk of developing a particular lung disease. In such a comparison, a concentration of a biomarker in the test sample that is the same or similar to the concentration of the biomarker in the standard identities the subject's risk of developing a preselected lung disease. In one aspect, a metabolite biomarker includes a metabolite derived from host-gut microflora symbiosis. In another aspect the metabolite biomarker is selected from formate, hippurate and/or trigonelline.

In one embodiment, the present disclosure provides a method of determining an increase in severity of lung disease in a subject. In one aspect, the method includes determining the concentration of one or more, or two or more biomarkers in a urine sample obtained from a subject diagnosed as having a lung disease, and correlating the level of expression of the one or more, or two or more biomarkers to known levels of expression in urine samples from subjects having known degrees of severity of a lung disease. In another aspect, the method includes a comparison of metabolic profiles of one or more, or two or more biomarkers in a subject's urine wherein the profiles are obtained at a first time point versus a second time point, and a difference in the metabolic profiles indicates an increase in severity of the subject's lung disease. In one aspect, a metabolite biomarker includes a metabolite derived from host-gut microflora symbiosis. In another aspect the metabolite biomarker is selected from formate, hippurate and/or trigonelline.

In an another embodiment, the metabolite biomarkers are useful as prognostic indicators of lung disease. In one aspect, the method includes determining the concentration of one or more, or two or more biomarkers in a urine sample obtained from a subject diagnosed as having a lung disease, and correlating the level of expression of the one or more, or two or more biomarkers to known levels of expression in urine samples from subjects having known degrees of severity of a lung disease. Thus, in one aspect, the present disclosure provides a method of determining the prognosis of a lung disease in a subject by detecting in a subject urine sample the presence of one or more, or two or more metabolite biomarkers at a first point in time and then at a second point in time, and comparing the profile of metabolite biomarkers present at the second time point versus the first time point to determine the prognosis of the lung disease in the subject. In one aspect the metabolite biomarker includes a metabolite derived from host-gut microflora symbiosis. In another aspect, the metabolite biomarker is selected from the group consisting of: formate, hippurate and trigonelline.

In one embodiment, the method comprises managing a subject's treatment based on the profile of one or more, or two or more biomarkers present in one or more urine samples obtained from the subject prior to, during and/or post-treatment for a lung disease. Managing the subject's treatment includes administering to the subject one or more suitable treatments consistent with the symptoms presented by the subject, the underlying cause of the subject's disease and/or the subject's specific needs and limitations. In a further embodiment, the method comprises observing or measuring at least one biomarker following administration of a treatment (e.g., a therapeutic agent) to a subject. Such observations or measurements can be used to track the progression of the subject's condition and/or treatment. In such embodiments the metabolite biomarker include a metabolites derived from host-gut microflora symbiosis. In another embodiment, the metabolite biomarker is selected from the group consisting of: formate, hippurate and trigonelline.

In other embodiments, the present disclosure provides a method of observing or measuring at least two, three, four, five, six, seven, eight, ten, twelve, fifteen, or sixteen or more different metabolite biomarkers in a urine or biofluid sample. In one particular embodiment, the metabolite biomarker includes a metabolite derived from host-gut microflora symbiosis. In another particular embodiment, the biomarkers include one or more, two or more or all three of: formate, hippurate and trigonelline.

Also provided are kits for use in the diagnosis, treatment, and evaluation of lung disease.

In one embodiment, the present disclosure provides the use of a biomarker for diagnosing, prognosing or monitoring lung disease, in a subject, comprising one or more metabolites selected from the group consisting of: formate, hippurate and trigonelline. In another particular embodiment, the metabolite is derived from host-gut microflora symbiosis. In another particular embodiment, the biomarkers further comprising at least one isotopically labeled form of formate, trigonelline or hippurate. Yet, in another particular embodiment, the at least a portion of one or more of formate, trigonelline or hippurate is present as an ester.

In another embodiment the present disclosure provides a method of monitoring lung function, monitoring the effect of a therapy while treating a lung disease condition in a subject, or determining the risk of developing a lung disease in a subject comprising: (a) observing one or more metabolite biomarkers in the subject's urine at a first time; and (b) observing said one or more metabolite biomarkers in the subject's urine at a second time. In another particular embodiment, the observing comprises determining a concentration or amount of at least one metabolite in the subject's urine, or the ratio of at least one of said one or more metabolites relative to either another component in the subject's urine or a standard added to the subject's urine. In another particular embodiment, the observing is conducted at least one second time. Yet, in another particular embodiment, the method further comprising determining if the concentration, amount or ratio of said one or more metabolites in the urine is outside of the normal range observed in the urine of an individual or population of individuals that does not have lung disease.

BRIEF DESCRIPTION OF THE DRAWINGS

FIG. 1 shows a urine NMR spectrum for a urine sample obtained from a subject having COPD. Water and urea peaks are omitted from the analysis. The other compounds are standardized to creatinine peaks. Peaks for compounds having association with baseline lung function are primarily in the aromatic region (see FIG. 2, expansion) and are marked with an asterisk "*". The bold peak at 4.0 ppm is hippurate; the bold peak at 4.4 ppm is trigonelline. Output is from Chenomix Profiler 5.0.

FIG. 2 shows an exemplary urine NMR spectrum showing an expansion of the aromatic region. The trigonelline peaks correspond to the significant bin at 8.81-8.87 ppm (see Table 4). The tall hippurate peaks (on right) correspond to the significant bins at 7.82-7.88, 7.62-7.66 and 7.51-7.57 ppm. The broad hippurate peak (on left) corresponds to the 8.50-8.56 and 8.56-8.61 ppm bins. Formate is typically lower in concentration than the other two compounds and corresponds to the significant bin at 8.43-8.48 ppm. Output is from Chenomx Profiler 5.0.

DETAILED DESCRIPTION

Metabolites present in a subject's extracellular fluid are in dynamic equilibrium with the subject's intracellular fluid as well as tissues. Consequently, abnormal cellular processes in a subject's tissues as a consequence of disease may be reflected as alterations in the subject's biofluid composition. The present disclosure provides methods of identifying metabolites that are useful as novel biomarkers of lung disease. Also provided are methods of using those novel biomarkers for diagnosis, aiding in the diagnosis, and prognosis of a subject's lung disease. In one embodiment, the disease is cigarette smoking-related COPD. In other embodiments, the lung disease includes, but is not limited to, obstructive pulmonary disease, chronic systemic inflammation, emphysema, asthma, pulmonary fibrosis, cystic fibrosis, obstructive lung disease, pulmonary and inflammatory disorder. In another embodiment, the lung disease is lung cancer.

Fluids secreted, excreted, or otherwise derived from an organism ("biofluids") allow a unique view into the diseased state of the organism because the compositions within a particular sample of biofluid reflect the functional status of the cells (and thereby, organs) of the organism. Altered or abnormal cellular processes within a diseased subject are reflected in the biochemical make up of biofluids sampled from the subject. Thus, analysis of metabolites present in a biofluid sample obtained from a subject (e.g., extracellular tissue fluid, blood, serum, plasma, sputum, saliva, or urine)

is useful for diagnosis, aiding in the diagnosis, prognosis, managing, and/or adjusting treatment of a lung disease in the subject. Furthermore, such analysis, as provided by the present disclosure, can be performed on standard preparations of samples obtained from a patient (e.g., serum, plasma, urine, CSF fluid, etc. . . . ), bypassing the need for special sampling methods and preparation of the biological sample (e.g., tissue biopsies).

As described herein, a "biomarker" or "metabolite biomarker" is a metabolite, or portion thereof, which is differentially present in a biofluid (e.g., urine) sample obtained from an individual having one phenotypic status (e.g., having a lung disease such as CORD) as compared with a biofluid (e.g., urine) sample obtained from an individual having another phenotypic status (e.g. healthy subject not having a lung disease). The biomarkers described herein may be used to identify, predict, or monitor a lung disorder or status of the lung disorder in the subject. A biomarker is also a metabolite, or portion thereof, that is used to monitor the effectiveness of a therapy for a lung disorder. A metabolite is a biomarker if it is differentially present between various phenotypic statuses and the presence or level (quantity or concentration) of the metabolite is significantly associated with a particular phenotype. In particular, the present disclosure is based in part on the discovery that certain metabolites are differentially present in urine of subjects suffering from COPD as compared to urine of subjects not having COPD. The metabolite composition within a biofluid sample obtained from a subject is also referred to as the subject's "metabolic phenotype".

In one embodiment an individual or a population of individuals may be considered as not having lung disease or impaired lung function when they do not have clinically relevant signs or symptoms of lung disease. Thus, in various aspects, an individual or a population of individuals may be considered as not having chronic obstructive pulmonary disease, chronic systemic inflammation, emphysema, asthma, pulmonary fibrosis, cystic fibrosis, obstructive lung disease, pulmonary inflammatory disorder, or lung cancer when they do not manifest clinically relevant symptoms and/or measures of those disorders. In one embodiment, an individual or a population of individuals may be considered as not having lung disease or impaired lung function, such as CORD, when they have a FEV1/FVC ratio greater than or equal to about 0.70 or 0.72 or 0.75. In another embodiment, an individual or population of individuals that may be considered as not having lung disease or impaired lung function are sex- and age-matched with test subjects (e.g., age matched to 5 or 10 year bands) current or former cigarette smokers, without apparent lung disease who have an FEV1/FVC≥0.70 or ≥0.75. Individuals or populations of individuals without lung disease or impaired lung function (control subjects) may be employed to establish the normal range of metabolites observed in urine or other biofluids, or to provide samples against which to compare one or more samples taken from a subject (e.g., samples taken from a subject at one or more different first and second times) whose lung disease or lung function status may be unknown. In other embodiments, an individual or a population of individuals may be considered as having lung disease or impaired lung function when they do not meet the criteria of one or more of the above mentioned embodiments.

In another embodiment, control subjects (subjects not having lung disease or impaired lung function), as used herein are sex- and age-matched current or former cigarette smokers, without apparent lung disease or impaired lung function who had FEV1/FVC≥0.70. Age matching may be conducted in bands of several years, including 5, 10 or 15 year bands. Control subjects are preferably recruited from the same clinical settings. A control group is more than one, and preferably a statistically significant number of control subjects. In another embodiment control subjects are sex- and age-matched (in 10 year bands) current or former cigarette smokers, without apparent lung disease or impaired lung function who had FEV1/FVC≥0.70.

In one embodiments biomarkers of lung function or lung disease may be identified using a method comprising:
 a) obtaining a profile of metabolites present in a biofluid sample from a subject at one or more preselected time point, wherein each profile is obtained using a high resolution nuclear magnetic resonance (NMR) method (and optionally a preselected spectral integral (bin)); and
 b) comparing each profile of the subject to a standard profile obtained from a control subject, wherein a statistical analysis of the subject profile relative to the standard profile identifies one or more metabolites as a biomarker of lung function.

In such methods the subject and the control subject can be assessed for one or more, two or more, or three or more, measures of lung function selected from the group consisting of: age-related decline (age decline), cigarette smoking-related decline (pack-years decline), intensifying effects of smoking with increasing age (CPD×Age decline), and a measure of baseline lung function at $T_0$ (an initial time or aka time zero). In one embodiment the biofluid sample is urine. Where biofluids are employed to identify biomarkers it may be advantageous for the samples to be normalized so that concentration differences, for example due to the hydration of the subject or control subjects may be taken into account. Where urine is employed as a biofluid, the sample may be normalized to a component present therein, for example creatinine.

Such methods of identifying biomarkers of lung function or lung disease may be used to identify markers for lung diseases including, but not limited to: COPD; chronic systemic inflammation, emphysema, asthma, pulmonary fibrosis, cystic fibrosis, obstructive lung disease, pulmonary inflammatory disorder, and lung cancer. Individual compounds that may be employed as biomarkers can be identified using any suitable technique, including but not limited to: liquid chromatography, gas chromatography, mass spectroscopy, gas chromatograph mass spectroscopy, liquid chromatograph mass spectroscopy, or nuclear magnetic resonance.

Due to the etiological complexity of lung disease, conventional analytical methods, such as use of spirometric measurements alone, to derive data for comparison of, e.g., COPD-affected/unaffected status suffer from inconsistent accuracy. The present disclosure provides novel metabolite biomarkers identified and/or characterized using a highly sensitive and accurate technique. In one embodiment, a metabolite biomarker is identified through use of NMR spectroscopy. The use of NMR spectroscopy to study compounds in biological fluids having low molecular weight is known in the art. See, e.g., Nicholson et al., 'High resolution proton magnetic resonance spectroscopy of biological fluids', *Progress in NMR Spectroscopy,* 21, 449-501, (1989); and Lindon et al., 'NMR spectroscopy of biofluids', *Annual reports on NMR spectroscopy,* 38 (1999). Exposure to toxins results in altered biochemical composition of body fluids, detectable by NMR spectroscopy. See, for example, Holmes et al. (*Nature*, vol. 453, no. 7193, pp. 396-400, 2008), 'NMR spectroscopy and pattern recognition analysis of the biochemical processes associated with the progression and recovery from nephrotoxic lesions in the rat induced by mercury (II) chloride and 2-bromoethanamine', *Mol. Pharmacol.*, 42, 922-930 (1992). The identified metabolites also increase etiological understanding of COPD and are useful as biomarkers of lung function and lung function decline. Thus, the present disclosure provides methods of identifying a biomarker of a lung disease and/or methods of using the biomarker for diagnosis, aiding in the diagnosis, or management of a lung disease.

An NMR spectrum provides a metabolite profile for the sample of biofluid analyzed. Such spectra represent a measure of all NMR detectable species present in the biofluid sample. As such, these spectra comprise a high density of data requiring statistical analysis to identify associations between a particular metabolite and lung disease. The metabolite profile is altered, for example, in conditions of a lung disease, such as, for example, COPD. A profile of metabolites present in a subject is a characteristic NMR spectrum of a biofluid sample obtained from the subject.

As used herein, the term "profile" or "metabolite profile" is a characteristic set of peaks or other NMR data of preselected metabolites present in a single biological fluid sample. Alternatively, a "profile" may be the amounts, concentrations, or relative concentrations of one or more preselected metabolites (metabolite biomarkers) in a biological fluid sample. A biological fluid sample may be a urine sample obtained from a single subject or may be a pooled sample comprising urine obtained from one or more subjects.

A difference in metabolite profile is defined as a characteristic set of NMR spectral lines within defined bins (integrated spectral regions) whose signal intensity values significantly differ between NMR spectra of metabolites in a biological fluid sample (e.g. urine) obtained from a subject having a lung disease (e.g. COPD) as compared to the NMR spectra of metabolites in a biological fluid sample (e.g. urine) obtained from a healthy subject or a pool of healthy subjects, or subjects not having the lung disease. Such a difference in profile comprises the spectral line positions within a defined bin and optionally their corresponding signal intensities or signal intensity differences.

NMR spectroscopy is also advantageous in that detectable metabolites present in a urine sample may be identified without prior knowledge of which specific metabolite is being characterized. Thus, by NMR spectroscopy, previously unrecognized biomarkers (metabolites) present in biofluids (e.g. urine) from individuals having different phenotypes may be identified. In addition to identification of new biomarkers, NMR spectroscopy assays may be automated allowing for analysis of hundreds of metabolites simultaneously (e.g., high-throughput NMR spectroscopy). Due to its high level of sensitivity, use of NMR spectroscopy can also provide a profile of metabolites using a sampling of biofluid (e.g. less than 0.3, or less than 0.5 or less than about 1.0 to 5.0 ml).

Approaches to analyzing NMR-based data include chemometric and quantitative approaches. Use of chemometric analysis does not require initial identification of significantly associated metabolites. Spectral patterns and intensities are compared to identify relevant spectral features distinguishing sample classes of metabolites. Subsequent statistical analysis is performed to identify those metabolites corresponding to preselected relevant features. Analysis of data may alternatively include use of targeted profiling (quantitative analysis) to identify and quantify NMR detectable metabolites prior to their subsequent data analysis, for determination of a significant association with one or more particular measure of lung function or decline in lung function. Exemplary methods for data analysis to calculate statistical significance include, among others, Ordinary least squares (OLS) regression to test associations between NMR spectrum region integrals (bins) and measures of lung function or lung function decline, wherein the measures of lung function or lung function decline are determined by $FEV_1$. In an embodiment, data analysis may include use of classification algorithm software known in the art. See, e.g., Xia et al., 'MetaboAnalyst: a web server for metabolomic data analysis and interpretation', *Nucleic Acid Res., July:* 37 (2009).

In one embodiment, identification of metabolites significantly associated with a lung disease includes the use of a statistical model wherein, for each measure of lung function and the $FEV_1$ residual (i.e. $FEV_1$, adjusted for the covariates of the best-fitting model), a separate simple regression is estimated for each bin, with the bin predicting the lung function measure. Exemplary measures of lung function include measure of baseline lung function at subject entry into the study, age-related decline (age decline), cigarette smoking-related decline (pack-years decline) and intensifying effects of smoking as measured by number of cigarettes/day on decline with increasing age (CPDxAge decline). In one embodiment, bin values may be adjusted for potential confounders (i.e., age, gender, smoking status and average cigarettes per day) using OLS regression analysis to establish that significant associations are not spurious due to other factors influencing metabolite profiles.

In one embodiment, a measure of lung function employs use of mixed modeling analysis of longitudinal spirometric data. Longitudinal data of lung function and various risk factors are analyzed to identify metabolites associated with lung function decline. The data include outcome measures of decreased lung function measured spirometrically as the forced expiratory volume in 1 second ($FEV_1$) (Knudson et al., 1983, *American Review of Respiratory Disease*, vol. 127, pp. 725-734). The four measures are derived by fitting mixed models to longitudinal spirometric, smoking history, and demographic data obtained over the subjects' 17-year average participation period in the NIH-sponsored Lung Health Study (LHS) and its follow-on Genetics of Addiction Project (GAP). Conceptually, these measures represent different underlying biological processes driving lung function decline. The optimal model of the data is selected based on likelihood ratio tests, which are used to determine the significance of each fixed and random effect parameter as it is added to the model (Willet et al. 1998, *Dev. Psychopathol.*, 10, 395-426). After the optimal model is identified, the outcome variables are calculated as best linear unbiased predictors (BLUPs) of the random effects, focusing on age-related decline (age decline), pack-years-related decline (pack-years decline), and the intensifying effects of smoking, in terms of number of cigarettes per day (CPD), on decline with age (CPDxage decline). These BLUPs together accounted for the vast majority of individual differences in lung function decline in these subjects. Baseline lung function (BL) measured at a subject's entry into the study is also included as an outcome measure as it varies across individuals (Griffith et al., 2001, *American Journal of Respiratory and Critical Care Medicine*, vol. 163, pp. 61-68).

In one embodiment, the present disclosure provides novel metabolite biomarkers that can be used for in vivo and/or in vitro medical diagnostics. A method of diagnosing or aiding in the diagnosis of lung disease in a subject is provided wherein the method includes determining the level of metabolite biomarkers in a sample of biofluid from the subject. In one aspect, the method includes observing or detecting in a urine sample obtained from a subject the presence of, or measuring the level or concentration of, one or more, or two or more metabolite biomarkers. In one embodiment, the metabolite biomarker(s) include a metabolite derived from host-gut microflora symbiosis. In another embodiment, the metabolite biomarker(s) are selected from the group consisting of: formate, hippurate and trigonelline.

Diagnosis of lung disease may include but is not limited to examination for the presence of one or more, or two or more, or three or more, biomarkers in a test sample obtained from a test subject, wherein the absence or reduction of one or more preselected metabolite biomarker of a lung disease in the urine sample, compared to a control biological fluid sample or standard, indicates the presence of lung disease in the test subject. In such a case, the test sample is a sample of urine from a subject whose disease status is unknown or who is suspected of having a lung disease. The control biological fluid sample may be urine from an individual or a population of individuals (pool) that is known to not to have lung disease.

Once metabolite biomarkers present in biofluids are identified, they can be used in a variety of methods including, but not limited to, methods of diagnosing lung disease, methods of providing a prognosis of (prognosing) lung disease, methods of monitoring lung function, and methods of determining a subject's risk of developing a lung disease. Lung disease include, but are not limited to, the group consisting of COPD, obstructive pulmonary disease, chronic systemic inflammation, emphysema, asthma, pulmonary fibrosis, cystic fibrosis, obstructive lung disease, pulmonary inflammatory disorder, and lung cancer.

Assessment of samples from subjects can be conducted on a one time basis to obtain observations of metabolites biomarkers such as formate, hippurate or trigonelline. Where single assessments/observations are conducted, data may be analyzed by comparing it to standard amounts, concentrations or ratios (normalized amounts) of the metabolites analyzed, where the standard amounts, concentrations or ratios have been obtained using samples from individuals, or a population of individuals, with and/or without lung diseases. Where multiple samples are obtained from a subject, they may be compared to each other to observe a trend (increasing or decreasing) in the concentration or amount of the metabolite biomarker.

In one embodiment, the present disclosure provides a method of using one or more metabolite biomarkers for diagnosing the presence of a lung disease or for determining a risk of developing a lung disease in a subject. A metabolite biomarker may include a metabolite derived from host-gut microflora symbiosis. In another aspect, the metabolite biomarker is selected from the group consisting of: formate, hippurate and trigonelline. A lung disease may include, for example, COPD, chronic systemic inflammation, emphysema, asthma, pulmonary fibrosis, cystic fibrosis, obstructive lung disease, pulmonary inflammatory disorder, and lung cancer, as well as other diseases of the lung. In one aspect the biological sample is a blood sample, a plasma sample, a serum sample, a urine sample, a lymphatic fluid sample, a sputum sample, or a saliva sample.

In another aspect, the status of a subject's lung disease may be determined by observing (e.g., measuring the quantity of) one or more particular biomarkers present in a biofluid sample from a subject who has been diagnosed with a particular lung disease, and correlating the quantity of each biomarker with a previously determined measure of the severity of the disease based on the presence of one or more particular biomarkers present in a previous test sample from the subject or on the quantity of each biomarker present in the previous test sample. A biomarker may include a metabolite derived from host-gut microflora symbiosis. In such an aspect, the metabolite biomarker is selected from the group consisting of: formate, hippurate and trigonelline.

As used herein, the term "status" refers to the degree of severity of a subject's lung disease such as, for example, the number or degree of severity of symptoms presented or exhibited by the subject suffering from the lung disease. The symptoms associated with different forms of lung diseases may differ between forms of lung diseases or may overlap. Exemplary symptoms commonly associated with COPD include long-term swelling in the lungs, destruction or decreased function of the air sacs in the lungs, cough producing mucus that may be streaked with blood, fatigue, frequent respiratory infections, headaches, dyspnea, swelling of extremities, and wheezing. A subject suffering from COPD may have a few to all of these symptoms. A subject suffering from an early stage of COPD can exhibit one, two, three, or a few symptoms.

In one embodiment, the present disclosure provides a method of determining the status of a subject's lung disease by assessing the level of expression of one or more metabolite biomarker during the course of the subject's lung disease. Such assessment includes (1) observing at a first time point, the level of expression of one or more biomarker(s) in a subject's sample, (2) observing the same biomarker(s) at a second time that occurs after said first time, and (3) comparing the first observation to the second observation, wherein a difference between the two observations indicates the status of the lung disease such as an increase or decrease in severity of the disease. In one embodiment a metabolite biomarker is a metabolite derived from host-gut microflora symbiosis. In another aspect, the metabolite biomarker is selected from the group consisting of formate, hippurate and trigonelline. Where the biomarker(s) are selected from the group consisting of formate, hippurate and trigonelline, a decrease in the amount of the biomarker(s) measured at second time is indicative of a decline in a subject's status.

In another embodiment the present disclosure provides a method for determining a subject's risk of developing a lung disease. In such a determination, the concentration or amount of one or more, or two or more metabolite biomarkers in a test sample is observed or measured and compared to a known standard. A standard may be a sample of urine obtained from an individual or a population pool having a known diagnosis of a lung disease or may be a fluid sample comprising a known concentration of one or more isolated biomarkers determined to be associated with a predetermined risk of developing a particular lung disease. In such a comparison, a concentration of a biomarker in the test sample that is the same or similar to the concentration of the biomarker in the standard identifies the subject's risk of developing a preselected lung disease. In one aspect, a metabolite biomarker includes a metabolite derived from host-gut microflora symbiosis. In another aspect the metabolite biomarker is selected from formate, hippurate and/or trigonelline. Where the biomarker(s) are selected from the group consisting of formate, hippurate and trigonelline, a decrease in the amount of those biomarker(s) measured, either relative to subjects without lung disease or as a function of time, is indicative of an increased risk of developing lung disease or expressing the symptoms of lung disease.

In an additional embodiment, the metabolite biomarkers are useful as prognostic indicators of lung disease and in methods of providing a prognosis of lung disease. In one aspect, the method includes observing (e.g. determining the concentration, level, or amount) of one or more, or two or more biomarkers in a urine sample obtained from a subject diagnosed as having a lung disease, and correlating the observation with observations of those biomarkers in urine samples from subjects having known degrees of severity of a lung disease. Thus, in one aspect, the present disclosure provides a method of determining the prognosis of a lung disease in a subject by detecting in a subject urine sample the presence of one or more, or two or more metabolite biomarkers at a first point in time and then at a second point in time, and comparing the profile of metabolite biomarkers present at the second time point versus the first time point to determine the prognosis of the lung disease in the subject. In one aspect, the metabolite biomarker includes a metabolite derived from host-gut microflora symbiosis. In another aspect, the metabolite biomarker is selected from the group consisting of: formate, hippurate and trigonelline. Where the biomarker(s) are selected from the group consisting of formate, hippurate and trigonelline, a decrease in the amount of those biomarker(s) measured, either relative to subjects without lung disease or as a function of time, is indicative of a prognosis of declining lung function or increased disease severity.

In one embodiment, the present disclosure provides a method of determining an increased risk that the symptoms of lung disease will increase in severity of lung disease in a subject. In one aspect, the method includes determining the concentration or amount of one or more, or two or more biomarkers in a urine sample obtained from a subject diagnosed as having a lung disease, and correlating the concentration or amount of the one or more, or two or mere biomarkers to known levels of expression in urine samples from subjects having known degrees of severity of a lung disease. In another embodiment, the method includes a comparison of metabolic profiles of one or more, or two or more biomarkers in a subject's urine wherein the profiles are obtained at a first time point versus a second time point, which occurs after said first time point, and a difference in the metabolic profiles indicates an increase or decrease in the severity of the subject's lung disease. In one aspect, a metabolite biomarker includes a metabolite derived from host-gut microflora symbiosis. In another aspect the metabolite biomarker is selected from formate, hippurate and/or trigonelline. Where the biomarker is selected from the group consisting of formate, hippurate and trigonelline, a decrease in the amount of the biomarker(s) measured at the second time is indicative of an increased risk of developing lung disease or an increase in the risk the symptoms of lung disease will increase in severity.

In another embodiment, the disclosure provides a method for managing a subject's treatment based on the profile of one or more metabolite biomarkers present in one or more urine samples obtained from the subject prior to, during and/or post-treatment (e.g., treatment for a lung disease). Managing the subject's treatment includes administering to the subject one or more suitable treatments consistent with the symptoms presented by the subject, the underlying cause of the subject's disease and/or the subject's specific needs and limitations. Exemplary therapeutic treatments for lung disease include administering to the subject one or more of immunosuppressants, corticosteroids (e.g. betamethasone delivered by inhaler), β2-adrenergic receptor agonists (e.g., short acting agonists such as albuterol), anticholinergics (e.g., ipratropium, or a salt thereof delivered by nebuliser), and/or oxygen. In addition, where the lung disease is caused or exacerbated by bacterial or viral infections, one or more antibiotics or antiviral agents may also be administered to the subject. In one aspect the metabolite biomarker includes a metabolite derived from host-gut microflora symbiosis. In a further aspect, the method comprises observing or measuring at least one biomarker following administration of a treatment to a subject. Such observations or measurements can be used to track the progression of the subject's condition and/or treatment. Where observations or measurements of metabolite biomarkers show that the treatments are not effective, the treatment regimen can be changed (e.g., to increase the dose, frequency, or type of therapeutic agent employed). Where observations or measurements show the treatment to be effective, the measurement can be understood to indicate that the therapy may be continued. Where observations or measurements show the therapy is only marginally or effective, the measurements may be taken to indicate that a change in the treatment may be necessary (e.g., a change in the dose frequency or therapeutic agent employed). In one aspect the metabolite biomarker includes a metabolite derived from host-gut microflora symbiosis. In one embodiment the metabolite biomarker is selected from the group consisting of: formate, hippurate and trigonelline.

In one embodiment, the present disclosure provides a method of diagnosing or prognosing lung disease in a subject, monitoring lung function or a lung disease, or determining a subject's risk of developing a lung disease, the method comprising observing/measuring one or more metabolites in the subject's urine at a first time.

Observing or observation(s), as used herein in reference to a metabolite biomarker, includes, but is not limited to, determining, the presence, concentration or amount (e.g., in grams or moles). Observing also includes measuring, detecting, quantitating a metabolite biomarker. Observing may be conducted by any means that allows assessing or determining the presence, concentration, level, or amount of one or more metabolites in the subject's urine or other biofluids. Several methods, including NMR, mass spectroscopy, and enzymatic assays are discussed below. A concentration or amount may be the total amount (e.g., in moles or grams) present in a given volume of urine or the amount in the urine produced by an individual (e.g., a subject) over a given time period such as a 24 hour period.

Metabolites (metabolic biomarker compounds) may be observed, measured, determined, quantitatated, compared or assessed by any method that can be used to detect or quantitate the metabolite compounds, or derivatives thereof (e.g. esters used gas chromatography). Such methods include, but are not limited to, liquid chromatography, gas chromatography, mass spectroscopy, gas chromatograph mass spectroscopy, liquid chromatograph mass spectroscopy, or nuclear magnetic resonance. Enzymatic and immuno assays that are specific to the metabolites may also be employed. (See e.g., Inagaki, H. 1994, *Int Arch Occup Environ Health*, 66(2):91-5)). Assays that measure the genes encoding proteins that are involved in the production of the metabolic biomarkers may also be employed.

In one embodiment, observing a metabolite is conducted by determining its concentration or amount relative to another component present in the urine as a ratio. This may be done, for example, to normalize the observation for the subject's hydration status. In one embodiment, normalization is conducted relative to creatinine so that a ratio of metabolite per unit of creatinine (metabolite/creatinine) is measured or assessed.

Once a concentration, amount or ratio of a metabolite is determined or measured, it may be compared to the concentration, amount or ratio of the same metabolite present in a sample from another subject, or it may be compared to normal ranges established for the metabolite biomarker in individuals not having lung disease. By such comparison it is possible to determine if the biomarker is outside of the normal range for individuals that do not have lung disease. Such comparisons can be used in methods of diagnosing lung disease, providing a prognosis of lung disease, or determining the risk that a subject will develop lung disease without taking further measurements of the metabolite. The information regarding the concentration of metabolite, such as formate, hippurate, or trigonelline, may be used in combination with other test results such as spirometric data to formulate the diagnosis or prognosis, or to evaluate a risk.

Methods of diagnosing or prognosing lung disease in a subject, monitoring lung function or a lung disease, or determining a subject's risk of developing a lung disease that comprise observing one or more metabolites in the subject's urine at a first time can also comprise monitoring one or more of the metabolites at one or more second times. The observations at one or more second times can be used in a variety of ways including, but not limited to, the development of trends in the direction of metabolite concentration for an individual subject that can be used as a prognostic indicator.

As used herein a first time is a time where a measurement of a metabolite is made in a sample from a subject, and a second time or times represent one or more times where a measurement of a metabolite is made (e.g., a sample is taken for measurement) following the measurement at the first time. A first time is not limited to the first measurement of a metabolite in a sample from a subject.

In one embodiment, a method of diagnosing lung disease or prognosing lung disease in a subject, monitoring lung function in a subject, or determining a subject's risk of developing a lung disease comprises:

(a) observing one or more metabolites in the subject's urine at a first time; and (b) observing one or more metabolites in the subject's urine at least one second time.

In such a method observing includes, but is not limited to, determining a concentration or amount of at least one metabolite in a subject's urine or determining the ratio of at least one of said one or more metabolites relative to either another component in said subject's urine or to a standard added to said subject's urine (e.g., a standard for quantitation of concentration/amount, chemical shift . . . ) at one or more of a first or a second time. Such methods may also comprise comparing a concentration, amount or ratio determined at a first or a second time to a concentration, amount or ratio of at least one of said one or more metabolites found in the urine of an individual or a population of individuals that does or does not have lung disease or impaired lung function (e.g., a value determined previously). In one embodiment, the metabolites are selected from hippurate, formate, and trigonelline.

In one embodiment, where a concentration, amount or ratio of one or more metabolites to another component (e.g., a ratio to creatinine for urine samples) determined in a sample from a subject at a first or a second time is less than a concentration, amount or ratio of at least one of said one or more metabolites found in the urine of an individual or a population of individuals that does not have lung disease or impaired lung function, the lesser concentration is indicative of a diagnosis of lung disease, a negative prognosis for lung disease, or an increased risk of developing a lung disease. In one embodiment, the metabolites having a lesser concentration at a second time are selected from hippurate, formate, and trigonelline.

In another embodiment, where a concentration, amount or ratio of said one or more metabolites determined in a sample from a subject at a second time is less than the concentration, amount, or ratio of said one or more metabolites determined in a sample from the subject at a first time, the lesser concentration at the second time is indicative of a diagnosis of lung disease, a negative prognosis for lung disease, or an increased risk of developing a lung disease. In one embodiment, the metabolites having a lesser concentration at a second time are selected from hippurate, formate, and trigonelline.

In methods where a metabolite is observed at a first time and at least one second time, the methods can include normalizing the concentration, amount or ratio of the metabolite to another compound in the urine sample, such as creatinine. Regardless of the method of diagnosing or prognosing lung disease in a subject, monitoring lung function in a subject, or determining a subject's risk of developing a lung disease, the one or more metabolites observed in a subject's urine may comprise: formate, trigonelline or hippurate, two or more of formate, trigonelline and hippurate; or formate, trigonelline and hippurate.

Another aspect of the subject matter described herein includes compositions of matter. In one embodiment, a composition comprises two or more of formate, trigonelline and hippurate. In another embodiment, the composition comprises formate, trigonelline and hippurate. Such compositions can be prepared to be free or substantially free of urea (e.g., they may comprise less than 2%, 1%, 0.5%, 0.1% or 0.01% of urea on a weight basis for dry compositions and or weight/volume for liquid compositions) and/or creatinine; as such, those compositions do not encompass urine. In one embodiment, the compositions comprise greater than 0.001%, 0.01%, 0.1%, 1%, 2%, 4%, 5% or 10% each of formate, trigonelline and hippurate on a weight basis for dry (solid) compositions or a weight/volume basis (e.g., g/ml) for liquid compositions.

In one embodiment, compositions comprising formate, trigonelline and/or hippurate further comprise a compound that can be used as a standard for determining either the chemical shift or the amount or concentration of a compound present in an analysis using NMR (e.g., 2,2',3,3'-deuterotrimethylsilylproprionic acid). Such compositions may also comprise a chemical shift agent so that peaks in the NMR spectra may be viewed without interference from peaks due to the resonances associated with other compounds.

In another embodiment, compositions comprising formate, trigonelline and/or hippurate may comprise at least one isotopically labeled form of formate, trigonelline, hippurate or another compound. For example, where analysis is to be conducted employing mass spectroscopy, the compositions may contain one or more compounds (e.g., one or more of formate, trigonelline and/or hippurate) labeled with one or more of $^{2}H$, $^{13}C$, $^{14}C$, $^{17}O$, $^{18}O$, or $^{15}N$.

In other embodiments, compositions comprising formate, trigonelline and/or hippurate may comprise at least a portion of one or more of formate, trigonelline or hippurate present as an ester or ether derivative. Such compositions may be employed for example as gas or liquid chromatography standards and may also comprise at least one compound that is labeled with $^{2}H$, $^{13}C$, $^{14}C$, $^{17}O$, $^{18}O$, or $^{15}N$.

Other aspects of the present invention are kits comprising one or more of the above-mentioned compositions. Such kits may further include instructions for the analysis of one or more of formate trigonelline or hippurate in urine or other fluids/biofluids or samples.

Also provided are kits for use in the diagnosis, treatment, and evaluation of lung disease. The materials and reagents required for observing or measuring one or more metabolite biomarkers of lung disease and providing a diagnosis or prognosis of a lung disease, or for use in the treatment or management of lung disease in a subject, may be assembled together in such a kit. In one embodiment, a kit for observing or measuring the level, concentration, or amount of a metabolite biomarker comprises materials including one or more enzymes specific for a preselected metabolite biomarker and/or at least one metabolite biomarker in one or more known concentrations; optionally the kit contains a control compound. Such kits may be used for diagnosing, identifying prognosis, or predicting a lung disease in a subject. Kits generally will comprise components and reagents for determining one or more biomarkers in a biological sample as well as control and/or standard samples. In some embodiments, the kit includes a pamphlet which includes a description of use of the kit in relation to COPD diagnosis or prognosis and instructions for analyzing results obtained using the kit.

Example 1

The below exemplary embodiments employ methods provided in the present disclosure for identification of novel biomarkers of lung function, lung function decline and lung disease, particularly COPD.

Materials and Methods

Subjects were selected from participants in the Lung Health Study (LHS) and Genetics of Addiction Project (GAP) at the University of Utah study center. LHS is a prospective, randomized, multicenter clinical study sponsored by the National Heart, Lung, and Blood Institute (NHLBI) which enrolled male and female otherwise healthy cigarette smokers, aged 35-60 years, with mild or moderate COPD during 1986-1989 (Connett et al. 1993, *Control. Clin. Trials,* 14, 3S-19S). Lung function was measured by spirometry as baseline, annually for 5 years, and once during 1998-2001. GAP is a follow-on study during 2003-2004 in which spirometry was performed, smoking status was assessed and plasma and urine samples for metabolomic analysis were obtained. Diet, exercise and alcohol intake were not assessed. One hundred ninety seven (197) subjects with COPD who had participated in LHS and GAP and, for comparison, 195 subjects without COPD (90 cigarette smokers and 105 never-smokers) enrolled in GAP were selected for study. Characteristics of the study groups are shown in Table 1. At the GAP assessment time point, 63% of the smokers with COPD and 48% of the smokers without COPD had quit smoking.

TABLE 1

Demographic, smoking history and lung function characteristics of the subjects

| Characteristic | Subjects With COPD (n = 197) | Subjects Without COPD (n = 195) | |
|---|---|---|---|
| | | Smokers (n = 90)[1] | Never-Smokers (n = 105) |
| Male, n (%) | 129 (66) | 42 (47) | 50 (48) |
| Age, mean (SD) | 64.7(6.20) | 57.2(6.96) | 56.8(8.13) |
| BMI (kg/m$^2$), mean (SD) | 28.6(3.53) | 28.5(7.05) | 29.5(7.72) |
| Cigarettes per Day, mean (SD)[1] | 20.4(11.84) | 19.5(11.74) | n/a |
| Years Smoked, mean (SD) | 38.0(9.97) | 32.5(12.24) | n/a |
| Pack-Years[3], mean (SD) | 57.5(30.13) | 45.1(27.85) | n/a |
| FEV$_1$ (L), mean (SD) | 2.15(0.658) | 3.05(0.735) | 3.19(0.856) |
| FEV$_1$ % predicted, mean (SD) | 69.4(17.09) | 101.8(14.13) | 102.3(16.46) |
| FEV$_1$/FVC, mean (SD) | 55.6(11.55) | 75.9(5.67) | 77.5(7.94) |

COPD, chronic obstructive pulmonary disease;
BMI, body mass index;
FEV1, forced expiratory volume in 1 s;
FVC. forced ventilatory capacity;
n/a, not applicable
[1]Daily cigarette consumption of continuing smokers. At the time of biosampling for metabolomic analysis, 114/180 (63%) of the smokers with COPD and 42/87 (48%) of the smokers without COPD had quit smoking (percentages based on non-missing responses).
[2]Pack-years = (average cigarettes smoked per day/20) × (years of smoking).

Measures of Lung Function and Decline

The outcomes in this analysis are four measures of lung function or decline in lung function measured spirometrically as forced expiratory volume in one second (FEV$_1$) (Knudson et al. 1983, *American Review of Respiratory Disease,* vol. 127, pp. 725-734). These four measures are derived by fitting mixed models to longitudinal spirometric, smoking and demographic data obtained over the subjects' 17-year average participation period in the LHS and GAP. Conceptually, three of these measures represent different underlying biological processes driving lung function decline. This study focused on age-related decline (age decline), cigarette smoking-related decline, as measured in pack-years (pack-years decline), and the intensifying effects of smoking, in terms of number of cigarettes per day (CPD), on decline with increasing age (CPD×Age decline). Together these three measures accounted for the vast majority of individual differences in lung function decline in these subjects. In addition, a measure of baseline lung function at subjects' entry into the study as an outcome is included as it varies considerably in magnitude among individuals (Griffith et al. 2001, *American Journal of Respiratory and*

*Critical Care Medicine*, vol. 163, pp. 61-68). The complete technical details for the derivation of these measures are provided below, and particularly in Example 2.

Blood and Urine Sampling and Preparation

Blood samples (4 mL) were obtained from each subject at least two hours after eating by venipuncture using a sodium citrated Vacutainer® tube. Within ten minutes of collection, blood was centrifuged at 1500 g and 2-6° C. for 15 minutes. The topmost plasma was removed and centrifuged at 1500 g for 15 minutes more. Plasma samples were shipped on dry ice, stored at −80° C., thawed just before analysis, and prepared in an adaptation of the method described by Tang et al. (Tang et al. 2004, *Anal. Biochem.*, vol. 325, no. 2, pp. 260-272). The NMR buffer used contained isotonic phosphate buffered saline (NERL Diagnostics, East Providence, R.I.), 20% $D_2O$, and 0.02% sodium azide. A 300 µl aliquot of each sample was diluted with 300 µl of prepared NMR buffer for a final concentration of 10% $D_2O$ and 0.01% sodium azide. 2,2',3,3'-deuterotrimethylsilylproprionic acid (TSP) was not used as an internal reference, due to interaction-induced baseline broadening that occurs in plasma samples (Tang et al. 2004). All samples were placed in a 5 mm NMR tube.

A 4 mL aliquot was obtained from a non-first morning urine sample from each subject. Urine samples were stored frozen at −80° C., and if necessary were shipped on dry ice. Samples were thawed just before analysis. A pH 7.2 buffer was prepared containing 200 mM sodium phosphate (Sigma-Aldrich, St. Louis, Mo.), 0.25 mM TSP (Sigma-Aldrich, St. Louis, Mo.), 0.025% sodium azide (Sigma-Aldrich, St. Louis, Mo.), and 25% deuterium oxide ($D_2O$; 99.9%, low paramagnetic, Cambridge Isotope Laboratories, Andover, Mass.). A 360 µl aliquot of urine was diluted with 240 µl of buffer to minimize pH variations. The final buffer concentration of the prepared samples was 80 mM sodium phosphate, 10% $D_2O$, 0.01% sodium azide, and 0.1 mM TSP. All samples were placed in 5 mm NMR tubes.

NMR Methods

NMR spectra were acquired on a Varian Inova 600 spectrometer (Varian Inc., Palo Alto, Calif.) at the Pacific Northwestern National Laboratory. The spectrometer system was outfitted with a Varian triple resonance cold probe and linked to a Sun Ultra 10 (Santa Clara, Calif.) workstation.

For each urine sample, a one-dimensional presaturation sequence with gradients (Varian "metab" pulse sequence) was collected. Final spectra were accumulations of 32 individual free-induction decays (FIDs). Each FID was obtained using a nonselective, 90-degree excitation pulse and digitized into 32K complex data points. A total inter-excitation pulse delay of 3.0 seconds was used, initiated by a gradient homogeneity spoil pulse to destroy residual transverse magnetization. The spectral width of 6980.8 Hz resulted in an acquisition time of 2.347 seconds for a total recycle time of 5.3 seconds.

For plasma samples, the Carr-Purcell-Meiboom-Gill (CPMG) pulse sequence with solvent presaturation was used in order to selectively suppress the spectral interferences from macromolecules such as proteins and lipoprotein particles. A total spin-echo time of 50 ms was used in the CPMG sequence. The data were accumulations of 32 FIDs. Each FID was induced using a nonselective, 90-degree excitation pulse and digitized into 32 K complex data points. The total inter-excitation pulse delay was 3.0 seconds. The spectral width of 7197.5 Hz resulted in an acquisition time of 2.276 seconds for a total recycle time of 5.3 seconds.

Data Processing

NMR spectra were processed using Advanced Chemistry Development (ACD) ID NMR Processor 11.0 (Advanced Chemistry Development Inc., Toronto, Canada). The ACD macro included a Fourier transform followed by automated phasing and baseline correction. Quality control was applied such that spectra with severely distorted baselines or poor water suppression were rejected. The regions below 0.5 ppm and above 9.0 ppm were excluded as they contained no spectral information. For plasma spectra, the region from 4.2 to 6.5 ppm was excluded to eliminate the residual water signal. For urine spectra, the region from 4.2 to 6.8 ppm was excluded to eliminate the signals from both the residual water and urea. Integration of spectra was performed using the intelligent binning algorithm in ACD 11.0, whereby bin widths were set to 0.04 ppm with a tolerance of 50% to allow for better bin positioning relative to observed peaks.

Statistical Analyses

Ordinary least squares (OLS) regression was used to test associations between NMR spectrum region integrals (bins) and the measures of lung function or lung function decline as measured by $FEV_1$. In the first set of analyses, the following procedure was used for each of the four lung function measures (see the section titled "Measures of lung function and decline" above) and the $FEV_1$ residual, i.e., $FEV_1$ adjusted for the covariates of the best-fitting model. A separate simple regression was estimated for each bin, with the bin predicting the lung function measure. In the second set of analyses, in order to establish that significant associations were not spurious due to other factors known to influence metabolomic profiles, bin values were adjusted for potential confounders (i.e., age, gender, smoking status and average cigarettes per day) using OLS regression, and the procedure described above was repeated.

After identifying robustly significant associations between bins and lung function measures, the compounds represented by the significant bins in urine were identified and quantified as described below. In addition to calculating concentrations for specific compounds, standardized concentrations were also calculated as ratios of the identified compounds to creatinine, in order to control for total metabolite concentration within each spectrum. In a third specification the creatinine-standardized concentrations were adjusted for age, gender and smoking. For each urine compound of interest, associations between all concentration specifications and the appropriate lung function measure were tested using OLS regression. As a final test of robustness, the sample was stratified into never-smokers and smokers (i.e. continuing and former cigarette smokers), and associations of compound concentrations to the appropriate lung function measures were examined in each group. All statistical analyses were carried out using Stata 9.2 (available on the world wide web at www-stata.com).

To control the risk of false discoveries, calculated for each p-value is a so-called q-value (Storey 2003, *Annals of Statistics no.* 31, pp. 2013-2035; Storey & Tibshirani 2003, *Proceedings of the National Academy of Sciences of the United States of America*, vol. 100, no. 16, pp. 9440-9445). A q-value an estimate of the proportion of false discoveries among all significant markers (i.e., q-values are false discovery rates or FDRs) when the corresponding p-value is used as the threshold for declaring significance. This FDR-based approach is preferred over traditional methods of multiple testing correction (van den Oord & Sullivan 2003) because it a) provides a good balance between the competing goals of finding true effects versus controlling false discoveries, b) allows the use of more similar standards in terms of the proportion of false discoveries produced across studies because it is much less affected by the number of (sets of) tests, which is an arbitrary factor, c) is relatively robust against correlated tests (Benjamini & Hochberg 1995, *Journal of the Royal Statistical Society B*, vol. 57, pp. 289-300; Brown & Russell 1997, *Statistics in Medicine*, vol. 16, no. 22, pp. 2511-2528; Fernando et al. 2004, *Genetics*, vol. 166, no. 1, pp. 611-619; Korn et al. 2004, *Journal of Statistical Planning and Inference*, vol. 124, no. 2, pp. 379-398; Sabatti, Service, & Freimer 2003, *Genetics*, vol. 164, no. 2, pp. 829-833; Storey 2003, *Annals of Statistics no.* 31, pp. 2013-2035; Tsai, Hsuch, & Chen 2003, *Biometrics*, vol. 59, no. 4, pp. 1071-1081; van den Oord 2005, *Molecular Psychiatry*, vol. 10, no. 3, pp. 230-231; van den Oord & Sullivan 2003, *Human Heredity*, vol. 56, no. 4, pp. 188-189) and d) gives a more subtle picture of the possible role of the tested markers, rather than an all-or-nothing conclusion about whether a study produces significant results.

Identification of Compounds in Urine

To identify the specific compounds in bins associated with the lung function measures, we inspected spectra using the Chenomx NMR Suite 5.0 (Chenomx Inc., Edmonton, Alberta, Canada). Compounds with signals in the spectral regions of the significant bins were examined and the assignments were made by quantitative fitting of the experimental spectra with reference spectra from the database using the Chenomx NMR Profiler software. Concentrations of highlighted compounds in urine spectra were assigned using the 0.1 mM TSP peak as a chemical shape and concentration reference.

Results

Examination of Spectral Integrals (Bins)

Each spectrum was checked for quality (flat baseline and no significant perturbation from the water suppression); 359 urine spectra (91.6%) and 362 T2 CPMG plasma spectra 92.3%) passed quality control. Those that failed were largely due to poor water suppression, causing problems with phasing. Intelligent binning yielded 148 bins per spectrum for urine and 177 for plasma.

Of the 148 bins generated for the urine spectra, several showed highly significant association with baseline lung function in the first set of analyses. As shown in Table 2, 12 bins were significant at q-value<0.1, and 30 at q-value<0.5. For the 12 significant bins at q<0.1, p-values ranged from $7.68 \times 10^{4}$ to $6.59 \times 10^{4}$. There were far fewer significant results for the other lung function measures in the urine analyses, with 6 bins significant at q<0.5 for CPD×age decline and 1 bin significant at q<0.3 for pack-years decline. There were no significant results for the $FEV_1$ residual and age decline in the urine analyses. As shown in Table 2, the only significant associations for the first set of plasma analyses were 12 bins associated with the $FEV_1$ residual measure at q<0.5.

TABLE 2

Number of significant associations between spectra bins and $FEV_1$ outcome measures for urine and plasma at various q-value thresholds. ($FEV_1$, forced expiratory volume in 1 s)

| Outcome | Urine (148 bins) | | | Plasma (177 bins) | | |
|---|---|---|---|---|---|---|
| measure* | q < 0.5 | q < 0.3 | q < 0.1 | q < 0.5 | q < 0.3 | q < 0.1 |
| Baseline lung function | 30 | 13 | 12 | 0 | 0 | 0 |
| Age Decline | 0 | 0 | 0 | 0 | 0 | 0 |
| Pack-years Decline | 1 | 1 | 0 | 0 | 0 | 0 |

TABLE 2-continued

Number of significant associations between spectra bins and $FEV_1$ outcome measures for urine and plasma at various q-value thresholds. ($FEV_1$, forced expiratory volume in 1 s)

| Outcome | Urine (148 bins) | | | Plasma (177 bins) | | |
|---|---|---|---|---|---|---|
| measure* | q < 0.5 | q < 0.3 | q < 0.1 | q < 0.5 | q < 0.3 | q < 0.1 |
| CPD × Age Decline | 6 | 0 | 0 | 0 | 0 | 0 |
| $FEV_1$ residual | 0 | 0 | 0 | 12 | 0 | 0 |

*See text for description.

To examine the extent to which the results might be driven by factors known to influence metabolomic profiles, bins were adjusted for potential confounders (i.e., age, gender, smoker/never-smoker status and average cigarettes per day). Results were robust, particularly for baseline lung function for which 16 bins (q<0.5) and 8 bins (q<0.1) were significant (Table 3). P-values for the latter 8 baseline lung function associations ranged from $4.80 \times 10^{-4}$ to $1.51 \times 10^{-4}$. Other significant associations included 3 bins for CPD×age decline (q<0.5) and 1 bin for pack-years decline (q<0.3). No significant associations remained between the plasma bin residuals and lung function measures after adjusting for potential confounders.

TABLE 3

Number of significant associations between spectra bin residuals (with the effects of age, gender and smoking status regressed out) and $FEV_1$ outcome measures for urine and plasma. ($FEV_1$, forced expiratory volume in 1 s)

| Outcome | Urine (148 bins) | | | Plasma (177 bins) | | |
|---|---|---|---|---|---|---|
| measure* | q < .5 | q < .3 | q < .1 | q < .5 | q < .3 | q < .1 |
| Baseline lung function | 16 | 15 | 8 | 0 | 0 | 0 |
| Age Decline | 0 | 0 | 0 | 0 | 0 | 0 |
| Pack-years Decline | 1 | 1 | 0 | 0 | 0 | 0 |
| CPD × Age Decline | 3 | 0 | 0 | 0 | 0 | 0 |
| $FEV_1$ residual | 0 | 0 | 0 | 0 | 0 | 0 |

*See text for description.

As shown in Table 4, the eight urine spectral bins with the strongest association with baseline lung function were the same before and after adjusting for potential confounders, suggesting that these were not spurious results driven by gender, age or cigarette smoking. However, the order of the top 8 bin-baseline lung function associations changed slightly, and the strength of the associations declined slightly, after adjusting for the effects of age, gender and smoking status. Further analyses (not shown) indicated that most of the attenuation in association strength was due to controlling for age.

TABLE 4

Specific urine spectra bins associated with Baseline lung function* at q < 0.1, ranked in order of significance.

| Raw (uncorrected) values | | | Residuals | | |
|---|---|---|---|---|---|
| Chemical shift (ppm) | p-value | q-value | Chemical shift (ppm) | p-value | q-value |
| 8.43-8.48 | 7.68E−05 | 0.007 | 8.81-8.87 | 0.0005 | 0.026 |
| 8.81-8.87 | 9.2E−05 | 0.007 | 8.56-8.61 | 0.0006 | 0.026 |

TABLE 4-continued

Specific urine spectra bins associated with Baseline lung function*
at q < 0.1, ranked in order of significance.

| Raw (uncorrected) values | | | Residuals | | |
|---|---|---|---|---|---|
| Chemical shift (ppm) | p-value | q-value | Chemical shift (ppm) | p-value | q-value |
| 8.56-8.61 | 0.0001 | 0.007 | 7.82-7.88 | 0.0009 | 0.026 |
| 8.50-8.56 | 0.0003 | 0.011 | 8.43-8.48 | 0.0009 | 0.026 |
| 7.51-7.57 | 0.0005 | 0.012 | 3.94-4.00 | 0.001 | 0.026 |
| 7.82-7.88 | 0.0005 | 0.012 | 7.51-7.57 | 0.0011 | 0.026 |
| 7.62-7.66 | 0.0006 | 0.012 | 7.62-7.66 | 0.0012 | 0.026 |
| 3.94-4.00 | 0.0008 | 0.015 | 8.50-8.56 | 0.0015 | 0.028 |
| 8.76-8.81 | 0.0019 | 0.031 | | | |
| 7.40-7.45 | 0.0037 | 0.052 | | | |
| 8.61-8.67 | 0.0039 | 0.052 | | | |
| 8.48-8.50 | 0.0066 | 0.081 | | | |

*See text for description.

Compound Assignment and Concentration Analyses for Urine

Figure 1:
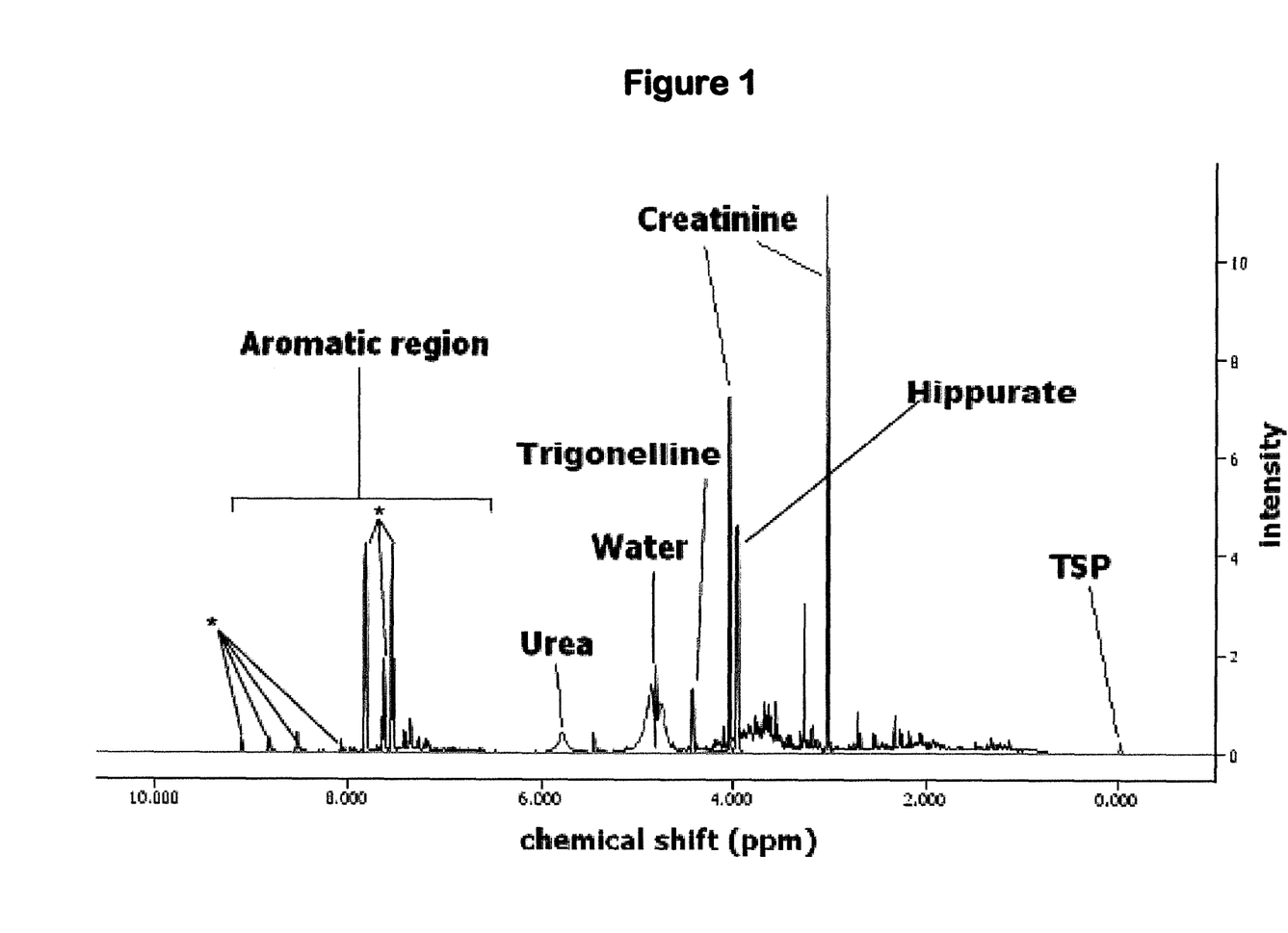
Figure 2:
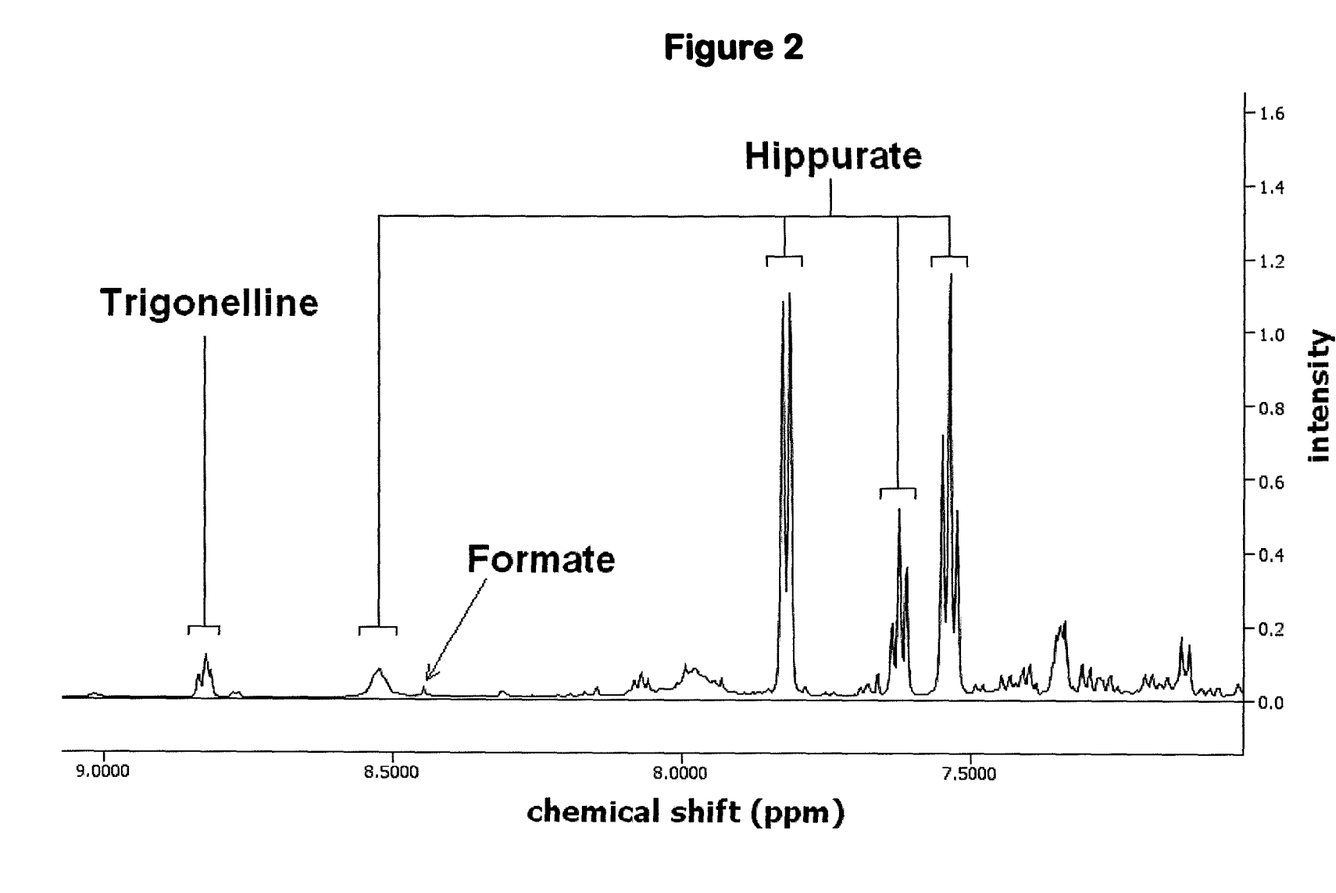

Examining the chemical shift range (measured in ppm) of the significant urine bins indicates that they are all located in the aromatic region, with one exception (Table 4). Using the Chenomx NMR Profiler, compounds in the regions of the 8 bins significantly associated with baseline lung function ($q<0.1$, confounders regressed out) were filtered, and manually assigned peaks within these bins to the best-fitting compounds. A complete example spectrum from a subject with COPD is shown in FIG. 1. The expansion of the aromatic region is shown in FIG. 2. The peaks for hippurate correspond to four of the top eight bins (Table 4, confounders regressed out). An additional broad peak for hippurate, located at approximately 8.5-8.6 ppm, could account for the significant bins found at 8.50-8.56 and 8.56-8.61 ppm. All predicted peaks for hippurate fell within a bin with $q<0.1$. The two remaining bins at 8.43-8.48 and 8.81-8.87 ppm correspond to formate and trigonelline, respectively. Formate yielded only a single peak such that all of its predicted peaks fell within a bin with $q<0.1$. While trigonelline is the most significant finding overall, other NMR signals from this compound did not fall in bins with $q<0.1$. Its predicted peaks at 9.1 ppm and 4.4 ppm are in regions that are excluded from the analysis. The remaining trigonelline peaks at 8.1 ppm did fall within the analyzed region but are not significant at the $q<0.1$ level. The reason for this appears to be overlap with other compounds, which potentially obscured the signal. Nevertheless, as shown in Table 5, all concentration specifications of these three compounds are significant at $p<0.05$, with the exception of the raw concentration for formate ($p=0.062$).

Trigonelline concentration showed the strongest association with baseline lung function, with all concentration specifications indicating a significant, positive relationship, such that higher urinary concentrations of trigonelline are associated with better lung function at baseline, adjusted for the effects of age, gender and smoking. For the most rigorous concentration specification—the creatinine-standardized residual—trigonelline exhibited strong association ($p=8.1\times10^{-4}$), explaining 3.2% of the variance in baseline lung function. Similarly, strong, positive relationships are found for baseline lung function and hippurate and formate concentrations. For the most rigorous creatinine-standardized residual concentration specification, associations are significant for both hippurate ($p=0.0052$) and formate ($p=0.0117$), with the two concentrations explaining 2.2% and 1.8% of baseline lung function, respectively. Finally, to eliminate the possibility that these findings are driven by the direct effects of smoking, the sample was stratified into smokers and never-smokers and associations of compound concentrations to baseline lung function in each group are examined. These results (not shown) indicate that the direction and general magnitude of the effects are consistent regardless of smoking status, although effect sizes are slightly larger among smokers.

The above described example indicates that the urinary metabolites trigonelline, hippurate and formate are associated with lung function. Measurements of those compounds (metabolite biomarkers) may be used to observe, diagnose or provide a prognosis of lung function decline. All significant associations are with the baseline lung function variable, which was derived from longitudinal $FEV_1$ measurements. The associations are found to be robust after adjusting for gender, age and cigarette smoking, thereby ruling out spurious findings due to these particular confounders. One cannot, however, rule out unmeasured confounders such as diet or lifestyle variables potentially affecting both lung function and these urinary metabolites and thereby accounting for the associations found in the present study. The analyses with plasma did not yield any metabolites significantly associated with lung function or lung function decline.

The clinical sampling of biofluids employed herein was subject to some limitations as compared to recent published guidelines (Sansone et al. 2007, *Nature Biotechnology*, vol. 25, no. 8, pp. 846-848). The urine collection was a single untimed spot collection rather than a first-morning void or a timed (e.g. 24-hour) collection. This may result in more inter-individual variability and a less robustly representative individual metabolic profile due to lack of control or standardization of diet, exercise and diurnal variation. However,

TABLE 5

Bivariate OLS regression results of Baseline lung function* regressed on compound concentrations

| | Compound Concentration Specifications | | | | | | | | |
|---|---|---|---|---|---|---|---|---|---|
| | Raw | | | Creatinine-Standardized | | | Standardized Residuals | | |
| | Coef | p-value | $R^2$ | Coef | p-value | $R^2$ | Coef | p-value | $R^2$ |
| Trigonelline | 0.223 | 0.0003 | 0.036 | 0.115 | 0.0002 | 0.038 | 0.12 | 0.0008 | 0.032 |
| Hippurate | 0.024 | 0.0042 | 0.023 | 0.017 | 0.0020 | 0.027 | 0.02 | 0.0052 | 0.022 |
| Formate | 0.468 | 0.0620 | 0.010 | 0.370 | 0.0034 | 0.024 | 0.34 | 0.0117 | 0.018 |

*See text for description.
Coef is correlation coefficient.

standardizing against creatinine concentrations were implemented to control for varying urine concentration due to hydration status. Even given the limitations on sampling, significant positive associations of urinary trigonelline, hippurate and formate with baseline lung function were observable, which adds credibility to the results and demonstrates the robustness of those biomarkers.

Blood was also sampled once, at least two hours post-prandially, but only limited diet and lifestyle information was collected. Nevertheless, insofar as the urinary results with trigonelline, hippurate and formate are true findings, negative results with these compounds in plasma are not surprising. None of these molecules are present at high concentrations in blood and would not have been readily detectable using $^1$H NMR under any sampling framework.

Hippurate, Formate and Trigonelline—Origins, the Gut Microbiome and Lifestyle Factors The biological origins of the urinary metabolites hippurate, formate and trigonelline are a mixture of endogenous production by human cells, production by the gut microbiome and dietary sources. Hippurate is formed as a result of conjugation between benzoate and glycine and is a gut microbial-mammalian co-metabolite (Li et al. 2008, *Proc. Natl. Acad. Sci. U.S.A*, vol. 105, no. 6, pp. 2117.2122; Nicholson, Holmes, & Wilson 2005, *Nat. Rev. Microbiol.*, vol. 3, no. 5, pp. 431-438). Diet is also a source of hippurate, and consumption of tea can lead to increases in urinary hippurate (Mulder, Rietveld, & Van Amelsvoort 2005, *Am J. Clin. Nutr.*, vol. 81, no. 1 Suppl, pp. 256S-260S). Endogenous formate is largely the product of one-carbon metabolism via the mitochondrial and cytosolic serine hydroxymethyl transferases and the tetrahydrofolate pathway (Gregory et al. 2000, *Am J. Clin. Nutr.*, vol. 72, no. 6, pp. 1535-1541). Formate is also produced as a byproduct of fermentation of dietary fiber by the gut microbiome (Holmes et al. 2008, *Nature*, vol. 453, no. 7193, pp. 396-400; Samuel & Gordon 2006, *Proc Natl Acad Sci U.S.A*, vol. 103, no. 26, pp. 10011-10016). Trigonelline, or 1-methylnicotinic acid, is formed endogenously by the methylation of the nitrogen atom of niacin (vitamin B3) and is ingested as part of a normal diet, being found in a variety of foodstuffs, including coffee (Kamanna & Kashyap 2008, *Am J. Cardiol.*, vol. 101, no. 8A, pp. 20B-26B; Lang et al. 2008, *J. Agric. Food Chem.* 56(23):11114-21).

An individual's metabolic profile or metabolic phenotype reflects complex interactions between the individual's genome and environmental factors, diet and symbiotic gut microbes (the microbiome) (Holmes et al. 2008, *Nature*, vol. 453, no. 7193, pp. 396-400). There is growing experimental evidence that inter-individual differences or disturbances in the gut microbiome can result in changes in the microbial-host metabolic balance with subsequent metabolic effects in the host that are associated with disease (Li et al. 2008, *Proc. Natl. Acad. Sci. U.S.A*, vol. 105, no. 6, pp. 2117-2122).

Relationships between gut microbiota and the development of diseases have been proposed for inflammatory bowel diseases, periodontal disease, rheumatoid arthritis, atherosclerosis, and allergy (Tlaskalova-Hogenova et al. 2004, *Immunol. Lett.*, vol. 93, no. 2-3, pp. 97-108). The longstanding hygiene hypothesis proposes that the microbial environment interfaces with and modulates the development of the host's immune system and subsequent risk of developing allergic and autoimmune diseases (Vercelli 2006, *Curr. Opin. Immunol.*, vol. 18, no. 6, pp. 733-737). Based on these observations and the metabolic origins of hippurate and trigonelline, it is possible that the urinary concentrations of these compounds in the test samples are indicative of variable gut microbiome compositions between individuals with differing lung function.

Unlike formate and hippurate, trigonelline does not originate from the gut microbiome, but is a breakdown product of niacin. Nevertheless, the urinary concentrations of trigonelline, hippurate and formate are highly correlated, with levels of all three being elevated in individuals with better baseline lung function. One explanation for this outcome is that a common mechanism underlies the detected levels of all three compounds, perhaps reflecting a complex composite "third variable". This could be the product of interactions between the host genome, diet and the gut microbiome, as well as environmental factors that are not, but may be, assessed, such as diet and lifestyle.

Example 2

Measures of Lung Function and Decline

The outcome variables used in these analyses were derived from random effects in linear mixed models analyzing longitudinal spirometric, smoking history, and demographic data (Goldstein, 1995, *Multilevel statistical models*. Wiley, New York). Specifically, data was modeled for 624 cigarette smokers with COPD and aged 35-60 at baseline, followed up 7 times over approximately 17 years (1986-2004) in the Lung Health Studies (Anthonisen et al., 1994, *JAMA*, 272, 1497-1505; Connett et al, 1993, *Controlled Clinical Trials*, 14, 3S-19S) and its follow-on Genetics of Addiction Project (GAP); 204 GAP subjects without COPD were also studied (see Table 6 for descriptive statistics). The optimal model of the data was selected based on likelihood ratio tests, which were used to determine the significance of each fixed and random effect parameter as it was added to the model (Willet et al., 1998, *Dev. Psychopathol.*, 10, 395-426). After the optimal model was identified, the outcome variables were calculated as best linear unbiased predictors (BLUPs) of the random effects. Missing data were handled by multiple imputation using chained equations, with 5 datasets imputed and analyzed (Van Buuren et al., 2006, *J. Stat. Comma. Sim.*, 76, 1049-1064; Royston, 2005, *S. J.*, 5, 527-536).

TABLE 6

Descriptive statistics of subject characteristics at study initiation*

| Variables | Female (N = 303) | | Male (N = 525) | |
|---|---|---|---|---|
| | Mean ± SD | Range | Mean ± SD | Range |
| Age (y) | 44.82 ± 8.08 | 26-60 | 46.59 ± 7.47 | 28-68 |
| $FEV_1$(L) | 2.44 ± 0.52 | 1.18-3.93 | 3.16 ± 0.63 | 1.02-6.09 |
| Height (cm) | 164.01 ± 5.88 | 150-180 | 176.89 ± 6.37 | 151-197 |
| Pack-years | 28.41 ± 20.44 | 0-87.5 | 38.14 ± 23.29 | 0-153 |

TABLE 6-continued

Descriptive statistics of subject characteristics at study initiation*

| Variables | Female (N = 303) | | Male (N = 525) | |
|---|---|---|---|---|
| | Mean ± SD | Range | Mean ± SD | Range |
| CPD | 0.58 ± 0.60 | 0-2.71 | 0.77 ± 0.67 | 0-4 |
| Never smoked | 0.21 | 0-1 | 0.09 | 0-1 |
| Total missing data, all variables and waves | 8.81% | | 8.73% | |

CPD, cigarettes per day.
Note:
Due to extremely small coefficient sizes, CPD was specified as CPD/20, thus making the measurement equivalent to packs per day; $FEV_1$, forced expiratory volume in 1 second; SD, standard deviation.
*Descriptive statistics calculated from non-imputed data at participant's first assessment.

In developing the random effect-based outcome measures, linear mixed models predicting $FEV_1$ were systematically developed. Linear mixed models are a generalization of linear regression allowing for the inclusion of random deviations (i.e. random effects) other than those associated with the overall residual term. In matrix notation, $$y = X\beta + Zu + \epsilon$$

where y is the n×1 vector of responses, X is a n×p design/covariate matrix for the fixed effect β, and Z is the n×q design/covariate matrix for the random effects u. The n×1 vector of residuals c, is assumed to be multivariate normal with mean zero and variance matrix $\sigma_e^2 I_n$.

The fixed portion, Xβ, is equivalent to the linear predictor of OLS regression. For the random portion, Zu+ϵ, it is assumed that the u has variance-covariance matrix G and that u is orthogonal to ϵ so that $$\mathrm{Var}\begin{bmatrix} u \\ \varepsilon \end{bmatrix} = \begin{bmatrix} G & 0 \\ 0 & \sigma_e^2 I_n \end{bmatrix}$$

The random effects u are not directly estimated (although, as described below, they may be predicted), but instead are characterized by the elements of G, known as the variance components, that are estimated along with the residual variance $\sigma_e^2$. Considering Zu+ϵ the combined error, we see that y is multivariate normal with mean Xβ and n×n variance-covariance matrix $$V = ZGZ' + \sigma e2 I n$$

The model building process is shown in Table 7. The outcome measures used in this analysis are derived from the random effects of the final, best-fitting model:

$$y_{ij} = \beta_0 + \beta_1 x_{1ij} + \beta_2 x_{2ij} + \beta_3 x_{3ij} + \beta_4 x_{4ij} + \beta_5 x_{5ij} + \beta_6 x_{6ij} + \beta_7 x_{7ij} + u_{0i} + u_{1i} + u_{2i} + u_{3i} + e_{ij}$$

where i indexes subjects, j indexes repeated assessments, y is $FEV_1$, $\beta_0$ is the intercept fixed effect, $x_1$ is age, $\beta_1$ is the age fixed effect, $x_2$ is pack years, $\beta_2$ is the pack years fixed effect, $x_3$ is CPD×age, $y_3$ is the CPD×age fixed effect, $x_4$ is height, $\beta_4$ is the height fixed effect, $x_5$ is gender, $\beta_5$ is the gender fixed effect, $x_6$ is gender×age, $\beta_6$ is the gender×age fixed effect, $x_7$ is never-smoked status, $\beta_7$ is the never-smoked status fixed effect, $u_{0i}$ is the intercept random effect, $u_{1i}$ is the age random effect, $u_{2i}$ is the pack years random effect, $u_{3i}$ is the CPD×age random effect and $e_{ij}$ is the within-subject residual. Parameter estimates and p-values for the final model (shown in Table 7 as Model 15) are shown in Table 8.

TABLE 7

Results of $FEV_1$ linear mixed modeling

| Model | Variables | Test statistic* | df† | vs. Model | p-value |
|---|---|---|---|---|---|
| 1 | Intercept | — | | — | — |
| 2 | Model 1 + Random Intercept | 2423.13 | 1, 41 | 1 | <.001 |
| 3 | Model 2 + Age | 992.28 | 1, 25 | 2 | <.001 |
| 4 | Model 3 + Random Age | 99.30 | 1, 159 | 3 | <.001 |
| 5 | Model 4 + Unstructured RE covariance | 122.74 | 1, 128 | 4 | <.001 |
| 6 | Model 4 + Age² | 2.48 | 1, 17 | 5 | NS |
| 7 | Model 5 + Height | 283.98 | 1, 110 | 5 | <.001 |
| 8 | Model 6 + Male | 26.38 | 1, 137 | 7 | <.001 |
| 9 | Model 7 + Male × Age | 15.00 | 1, 1144 | 8 | <.001 |
| 10 | Model 8 + Height × Age | 3.80 | 1, 65 | 9 | NS |
| 11 | Model 8 + Pack-years | 14.56 | 1, 6 | 9 | <.01 |
| 12 | Model 10 + Random Pack-years | 51.35 | 1, 7 | 11 | <.001 |
| 13 | Model 11 + CPD × Age | 7.89 | 1, 7 | 12 | <.05 |
| 14 | Model 11 + Random CPD × Age | 27.96 | 1, 18 | 13 | <.001 |

TABLE 7-continued

Results of FEV₁ linear mixed modeling

| Model | Variables | Test statistic* | df† | vs. Model | p-value |
|---|---|---|---|---|---|
| 15 | Model 12 + Never smoked | 104.69 | 1, 248 | 14 | <.001 |
| 16 | Model 13 + CPD | 1.03 | 1, 41 | 15 | NS |
| 17 | Model 13 + Pack-years × Age | 0.46 | 1, 164 | 15 | NS |
| 18 | Model 13 + Never smoked × Age | 0.36 | 1, 19779 | 15 | NS |

CPD, cigarettes per day.
Note:
Due to extremely small coefficient sizes, CPD was specified as CPD/20, thus making the measurement equivalent to packs per day; FEV₁, forced expiratory volume in 1 second; RE, random effect; NS, not significant.
*This is the multiple imputation version of the likelihood ratio test statistic (Allison, 2002, *Missing data*. Sage Publications, Inc., Thousand Oaks, CA; Li et al., 1991, *JASA*, 86, 1065-1073). The test statistic approximates an F-distribution under the null hypothesis. See Bollen and Curran (2006, *Journal of the Royal Statistical Society B*, vol. 57, pp. 289-300) for test statistic and degrees of freedom equations.
†Two values are given for the degrees of freedom as the test statistic has an F-distribution.

TABLE 8

Parameter estimates and statistical significance of final linear mixed model of FEV₁

| Fixed Effects | Parameters | SE | p-value |
|---|---|---|---|
| Intercept (L) | 2.960 | 0.047 | <.001 |
| Age (y) | −0.027 | 0.002 | <.001 |
| Height (cm) | 0.031 | 0.002 | <.001 |
| Male Gender | 0.542 | 0.055 | <.001 |
| Height × Age | −0.009 | 0.002 | <.001 |
| Pack-years | −0.002 | 0.001 | <.05 |
| CPD × Age | −0.003 | 0.000 | <.01 |
| Never smoked | 0.780 | 0.064 | <.001 |
| Random Effects | | | |
| SD (Intercept) | 0.505 | 0.031 | <.001 |
| SD (Age) | 0.021 | 0.001 | <.001 |
| SD (Pack-years) | 0.008 | 0.002 | <.001 |
| SD (CPD × Age) | 0.007 | 0.001 | <.001 |

CPD, cigarettes per day.
Note:
Due to extremely small coefficient sizes, CPD was specified as CPD/20, thus making the measurement equivalent to packs per day; FEV₁, forced expiratory volume in 1 second; SD, standard deviation; SE, standard error.

The covariance structure of the four random effects was modeled as unstructured:

$$\begin{bmatrix} u_{0i} \\ u_{1i} \\ u_{2i} \\ u_{3i} \end{bmatrix} \sim N(0, G)$$

with $$G = \begin{bmatrix} \sigma_{u0}^2 & & & \\ \sigma_{u10} & \sigma_{u1}^2 & & \\ \sigma_{u20} & \sigma_{u21} & \sigma_{u2}^2 & \\ \sigma_{u30} & \sigma_{u31} & \sigma_{u32} & \sigma_{u3}^2 \end{bmatrix}$$

Thus, the random parameters are multivariate normal distributed with means of zero and variance-covariance matrix G. The variances of the parameters are on the diagonal and the covariances in the off-diagonal cells of G. The residual was assumed to be normally distributed with a mean of zero and variance of $\sigma_e^2$.

Because random effects are not directly estimated by the mixed model, they must be predicted in an additional post-estimation step. BLUPs of the random effects u are obtained as $$\tilde{u} = \tilde{G} Z' \tilde{V}^{-1} (y - X\hat{\beta})$$

where $\tilde{G}$ and $\tilde{V}$ are G and V with estimates of the variance components plugged in. The EM algorithm was used for maximum likelihood estimation as described by Pinheiro and Bates (2000, *Mixed-effects models in S and S-plus*. Springer, New York).

Substitutions, modifications, changes and omissions may be made in the design, operating conditions and arrangement of the aspects and embodiments described herein without departing from the spirit of the disclosure as expressed, inter alia, in the appended claims. Additional advantages, features and modifications will readily occur to those skilled in the art. Therefore, the methods in their broader aspects are not limited to the specific details, and representative devices, shown and described herein. Accordingly, various modifications may be made without departing from the spirit or scope of the general inventive concept as defined, inter alia, by the appended claims and their equivalents.

All of the references cited herein, including patents, patent applications, and publications, are hereby incorporated in their entireties by reference.

The claims below are not restricted to the particular embodiments described herein. The following example is described for illustrative purposes and is not intended to limit the methods and compositions of the present disclosure in any manner. Those of skill in the an will recognize a variety of parameters that can be changed or modified to yield the same results.

The invention claimed is:

1. A composition that comprises less than 0.01% on a weight basis of urea and less than 0.01% on a weight basis of creatinine and greater than 0.5% by weight of each of two or more of formate, trigonelline and hippurate, wherein at least a portion of one or more of the formate, trigonelline or hippurate is present as an ester, with the proviso that the composition is not urine.

2. A composition comprising greater than 0.01% on a weight basis for dry compositions, or on a weight-to-volume (g/ml) basis for liquid compositions, of each of two or more of formate, trigonelline and hippurate, wherein one or more of formate, trigonelline and hippurate is labeled with one or more of $^2H$, $^{13}C$, $^{14}C$, $^{17}O$, $^{18}O$, or $^{15}N$, with the proviso that the composition is not urine.

3. The composition of claim 2, comprising greater than 0.1% on a weight or weight-to-volume (g/ml) basis of each of formate, trigonelline and hippurate.

4. A composition that comprises less than 0.01% on a weight basis of urea and less than 0.01% on a weight basis of creatinine and greater than 0.5% by weight of each of two or more of formate, trigonelline and hippurate, and further comprising at least one isotopically labeled form of formate, trigonelline or hippurate.

5. A composition that comprises less than 0.01% on a weight basis of urea and less than 0.01% on a weight basis of creatinine and greater than 0.01% by weight of each of two or more of formate, trigonelline and hippurate, wherein at least a portion of the formate is present as an ester.

6. A kit comprising the composition of claim 1.

7. The composition of claim 1 that is free of urea and creatinine comprising known amounts of formate, trigonelline and hippurate.

8. The composition of claim 2, wherein one or more of formate, trigonelline and hippurate is labeled with one or more of $^2H$, $^{14}C$, $^{17}O$, $^{18}O$, or $^{15}N$.

9. A method of detecting two or more of formate, trigonelline and hippurate in a urine sample, the method comprising:
  obtaining a urine sample; and
  detecting two of formate, trigonelline and hippurate in the urine sample by liquid chromatography, gas chromatography, mass spectroscopy, gas chromatograph mass spectroscopy, liquid chromatograph mass spectroscopy, or nuclear magnetic resonance and determining the amount of formate, trigonelline and/or hippurate in the sample by either comparison of the urine sample to the composition of claim 1 or claim 2, or by addition of the composition of claim 1 or claim 2 to the urine sample.

10. The method of claim 9, wherein the composition is the composition of claim 2.

11. The method of claim 10, wherein detecting two or more of formate, trigonelline and hippurate is conducted by mass spectroscopy, gas chromatograph mass spectroscopy, or liquid chromatograph mass spectroscopy.

12. The method of claim 9, wherein detecting two or more of formate, trigonelline and hippurate is conducted by nuclear magnetic resonance.

13. The method of claim 9, wherein the composition is the composition of claim 1.

* * * * *